(12) United States Patent
Boehringer et al.

(10) Patent No.: US 7,683,079 B2
(45) Date of Patent: Mar. 23, 2010

(54) 4-AMINOPIPERIDINE DERIVATIVES

(75) Inventors: Markus Boehringer, Moehlin (CH); Daniel Hunziker, Moehlin (CH); Bernd Kuhn, Liestal (CH); Bernd Michael Loeffler, Zug (CH); Thomas Luebbers, Loerrach (DE); Fabienne Ricklin, Hombourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 438 days.

(21) Appl. No.: 11/300,206

(22) Filed: Dec. 14, 2005

(65) Prior Publication Data

US 2006/0135561 A1 Jun. 22, 2006

(30) Foreign Application Priority Data

Dec. 20, 2004 (EP) .................................. 04106711

(51) Int. Cl.
*A61K 31/451* (2006.01)
(52) U.S. Cl. .................. 514/329; 514/319; 546/205; 546/223
(58) Field of Classification Search ................ 546/192, 546/195, 194, 205, 207, 223; 514/317, 319, 514/326, 329
See application file for complete search history.

(56) References Cited

U.S. PATENT DOCUMENTS

| | | | |
|---|---|---|---|
| 3,574,215 A * | 4/1971 | Lindenmann et al. ......... 546/65 |
| 3,681,361 A * | 8/1972 | Lindenmann et al. ....... 546/216 |
| 3,899,494 A * | 8/1975 | Ott et al. ...................... 546/65 |
| 4,367,232 A | 1/1983 | Boix-Igleasias et al. |
| 6,011,155 A | 1/2000 | Villhauer |
| 6,110,949 A | 8/2000 | Villhauer |
| 6,303,661 B1 | 10/2001 | Demuth et al. |
| 6,319,893 B1 | 11/2001 | Demuth et al. |
| 6,436,952 B1 * | 8/2002 | Flockerzi .................... 514/292 |
| 2002/0071838 A1 | 6/2002 | Demuth et al. |
| 2004/0209948 A1 | 10/2004 | Guan et al. |
| 2005/0107309 A1 | 5/2005 | Demuth et al. |
| 2005/0209274 A1 | 9/2005 | Lynch et al. |

FOREIGN PATENT DOCUMENTS

| | | |
|---|---|---|
| DE | 19616486 | 10/1997 |
| DE | 19834591 | 2/2000 |
| EP | 0 092 391 | 10/1983 |
| EP | 0 187 122 | 7/1986 |
| EP | 0 252 005 | 1/1988 |
| WO | WO 98/19998 | 5/1998 |
| WO | WO 99/38501 | 8/1999 |
| WO | WO 00/34241 | 6/2000 |
| WO | WO 01/40180 | 6/2001 |
| WO | WO 01/55105 | 8/2001 |

OTHER PUBLICATIONS

K. Hohenlohe-Oehringer, 3-Phenyl-aminopiperidin und am Ring-N alkylierte Abkommlinge, Mh. Chem., 96, 262-265.*
Hohenlohe-Oehringen, Monatshefte fuer Chemie 1965, 96(1), 262-5.*
Lazny R., et al., Synthesis, vol. 2003, No. 19, pp. 2858-2864.

* cited by examiner

*Primary Examiner*—Bernard Dentz
*Assistant Examiner*—David E Gallis
(74) *Attorney, Agent, or Firm*—George W. Johnston; Dennis P. Tramaloni; Samuel H. Megerditchian

(57) ABSTRACT

The present invention relates to compounds of the formula (I)

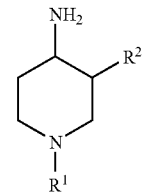

wherein $R^1$ and $R^2$ are as defined in the description and claims, and pharmaceutically acceptable salts thereof. The compounds are useful for the treatment and/or prophylaxis of diseases which are associated with DPP-IV, such as diabetes, non-insulin dependent diabetes mellitus and/or impaired glucose tolerance, obesity, and/or metabolic syndrome or β-cell protection.

11 Claims, No Drawings

4-AMINOPIPERIDINE DERIVATIVES

PRIORITY TO RELATED APPLICATIONS

This application claims the benefit of European Application No. 04106711.7, filed Dec. 20, 2004, which is hereby incorporated by reference in its entirety.

FIELD OF THE INVENTION

The present invention is directed to, for example, novel 4-aminopiperidine derivatives, their manufacture and their use as medicaments.

For example, the invention is directed to compounds of the formula (I)

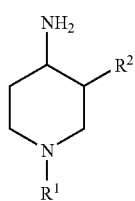

I and pharmaceutically acceptable salts thereof.

All documents cited or relied upon below are expressly incorporated herein by reference.

BACKGROUND OF THE INVENTION

The enzyme dipeptidyl peptidase IV EC.3.4.14.5 (EC is the abbreviation for "Enzyme Committee" of the International Union of biochemistry this enzyme is abbreviated in the following as DPP-IV) is involved in the regulation of the activities of several hormones. In particular DPP-IV efficiently and rapidly degrades glucagon like peptide 1 (GLP-1), which is one of the most potent stimulator of insulin production and secretion. Inhibiting DPP-IV would potentiate the effect of endogenous GLP-1, and lead to higher plasma insulin concentrations. In patients suffering from impaired glucose tolerance and type 2 diabetes mellitus, higher plasma insulin concentration would moderate the dangerous hyperglycemia and accordingly reduce the risk of tissue damage. Consequently, DPP-IV inhibitors have been suggested as drug candidates for the treatment of impaired glucose tolerance and type 2 diabetes mellitus (e.g. Villhauer, WO98/19998). Other related documents are WO 99/38501, DE 19616486, DE 19834591, WO 01/40180, WO 01/55105, U.S. Pat. No. 6,110,949, WO 00/34241 and U.S. Pat. No. 6,011,155.

SUMMARY OF THE INVENTION

In one embodiment of the present invention, provided is a compound of the formula I:

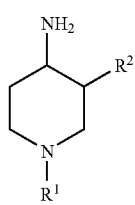

I wherein:

$R^1$ is selected from the group consisting of phenyl, unsubstituted or mono-, di-, or trisubstituted, independently, by lower alkyl, lower alkoxy, phenyl, phenoxy, halogen, or lower halogenalkyl;

naphthyl, unsubstituted or mono-, di-, or trisubstituted, independently, by lower alkyl, halogen, lower halogenalkyl, lower alkoxy, phenyl or phenoxy;

tetrahydronaphthyl;

$C_{3-7}$-cycloalkyl;

—$(CHR^3)_m$-phenyl, wherein m is 1, 2, or 3 and phenyl being unsubstituted or mono-, di, or trisubstituted, independently, by lower alkyl, halogen, lower halogenalkyl, lower alkoxy, phenyl or phenoxy and wherein $R^3$ is hydrogen, lower alkyl or phenyl;

—$(CH_2)_n$-heteroaryl, wherein n is 1, 2 or 3;

—$(CH_2)_n$-heteroaryl, wherein n is 1, 2, 3 and heteroaryl is mono-, di-, or trisubstituted, independently, by lower alkyl, halogen, lower halogenalkyl, or lower alkoxy;

—C(O)—$CH_2$-phenyl, with phenyl being unsubstituted or mono-, di-, or trisubstituted, independently, by lower alkyl, halogen, lower halogenalkyl, lower alkoxy, phenyl or phenoxy;

—C(O)—$CH_2$-heteroaryl; and

—C(O)—$CH_2$-heteroaryl, wherein heteroaryl is mono-, di-, or trisubstituted, independently, by lower alkyl, halogen, lower halogenalkyl, or lower alkoxy;

$R^2$ is selected from the group consisting of lower alkyl, lower halogenalkyl;

phenyl, unsubstituted or mono-, di-, or trisubstituted, independently, by lower alkyl, halogen, lower halogenalkyl, or lower alkoxy;

naphthyl, unsubstituted or mono-, di-, or trisubstituted, independently, by lower alkyl, halogen, lower halogenalkyl, or lower alkoxy;

heteroaryl, unsubstituted or mono-, di-, or trisubstituted, independently, by lower alkyl, halogen, lower halogenalkyl, or lower alkoxy;

—COOH;

—C(O)—$NR^4R^5$; wherein $R^4$ and $R^5$ are lower alkyl or together with the nitrogen atom to which they are attached form a 4-, 5- or 6-membered heterocycle which may contain a further heteroatom selected from O, N or S;

and pharmaceutically acceptable salts thereof.

In another embodiment of the present invention, provided is a process for the manufacture of compounds of formula I, comprising the steps of:

converting a compound of the formula

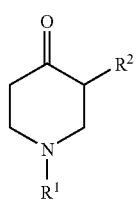

II wherein $R^1$ and $R^2$ are as defined above,
with hydroxylamine or a salt thereof into an oxime of the formula

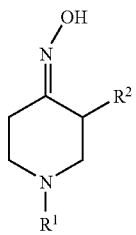

III wherein $R^1$ and $R^2$ are as defined above,
and further reducing the oxime of formula III by catalytic hydrogenation or alternatively by a reduction with a metal hydride into the compound of formula I; or
deprotecting an 4-aminopiperidine derivative of the formula

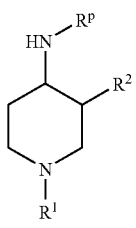

IV wherein $R^1$ and $R^2$ are as defined above and $R^P$ is an amino protecting group.

In a further embodiment of the present invention, provided is a pharmaceutical composition, comprising a therapeutically effective amount of a compound according to formula I and a pharmaceutically acceptable carrier and/or adjuvant.

In a yet another embodiment of the present invention, provided is a method for the treatment and/or prophylaxis of diseases which are associated with DPP-IV, comprising the step of administering a therapeutically effective amount of a compound according to formula I to a human being or animal in need thereof.

DETAILED DESCRIPTION

Provided herein are novel DPP-IV inhibitors that very efficiently lower plasma glucose levels. Consequently, the compounds of the present invention are useful for the treatment and/or prophylaxis of diabetes, particularly non-insulin dependent diabetes mellitus, and/or impaired glucose tolerance, as well as other conditions wherein the amplification of action of a peptide normally inactivated by DPP-IV gives a therapeutic benefit. In addition, the compounds of the present invention can also be used in the treatment and/or prophylaxis of obesity, metabolic syndrome, β-cell protection, autoimmune diseases such as inflammatory bowel disease, encephalitis periaxialis scleroticans and rheumatoid arthritis, Colitis Ulcerrosa, Morbus Crohn, psoriasis, lichen planus and/or benign prostate hypertrophy. The compounds may also be useful for the prevention of AIDS (acquired immunodeficiency syndrome) or for the preventing metastasis, particularly preventing metastasis of breast and prostate cancer to lung. Furthermore, the compounds of the present invention can be used as diuretic agent and for the treatment and/or prophylaxis of hypertension.

The compounds of the present invention exhibit improved therapeutic and pharmacological properties compared to other DPP-IV inhibitors known in the art, such as e.g. in context of pharmacokinetics and bioavailability.

Unless otherwise indicated, the following definitions are set forth to illustrate and define the meaning and scope of the various terms used to describe the invention herein.

In this specification the term "lower" is used to mean a group consisting of one to six, preferably of one to four carbon atom(s).

The term "halogen" refers to fluorine, chlorine, bromine and iodine, with fluorine and chlorine being preferred. Most preferred halogen is chlorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "lower alkyl" or "$C_{1-6}$-alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

Preferable lower alkyl residues are methyl ethyl, n-propyl and n-butyl, with methyl being especially preferred.

The term "lower halogenalkyl" refers to a lower alkyl group wherein at least one of the hydrogens of the lower alkyl group is replaced by a halogen atom, preferably fluoro or chloro, most preferably fluoro. Among the preferred lower halogenalkyl groups are trifluoromethyl, difluoromethyl, fluoromethyl and chloromethyl, with trifluoromethyl being especially preferred.

The term "alkoxy" refers to the group R'—O—, wherein R' is alkyl. The term "lower alkoxy" refers to the group R'—O—, wherein R' is lower-alkyl. Examples of lower alkoxy groups are e.g. methoxy, ethoxy, propoxy, isopropoxy, butoxy, isobutoxy and hexyloxy, with methoxy being especially preferred.

The term "cycloalkyl" or "$C_{3-7}$-cycloalkyl" refers to a monovalent carbocyclic radical of three to seven carbon atoms. This term is further exemplified by radicals such as cyclopropyl, cyclobutyl, cyclopentyl, cyclohexyl and cycloheptyl, with cyclopropyl and cyclohexyl being preferred.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e.g. indole or quinoline, or partially hydrogenated bicyclic aromatic groups such as e.g. indolinyl. Preferred heteroaryl groups are thienyl, pyridyl and indolyl, which can optionally be substituted as described above, preferably with lower alkyl or halogen.

The term "$R^4$ and $R^5$ together with the nitrogen atom to which they are attached form a 4-, 5-, or 6-membered heterocycle which may contain an additional heteroatom selected from O, N or S" means that $R^4$ and $R^5$ together with the nitrogen atom form a ring such as pyrrolidinyl, dihydropyrrolyl (pyrrolinyl), piperidyl, imidazolidinyl, morpholinyl, piperazinyl, thiazolidinyl, thiomorpholinyl, with thiazolidinyl and dihydropyrrolyl being especially preferred.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

The invention relates to compounds of the formula (I)

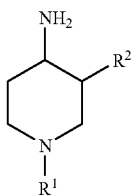

I wherein
$R^1$ is selected from the group consisting of
phenyl, unsubstituted or mono-, di-, or trisubstituted, independently, by lower alkyl, lower alkoxy, phenyl, phenoxy, halogen or lower halogenalkyl;
naphthyl, unsubstituted or mono-, di-, or trisubstituted, independently, by lower alkyl, halogen,
lower halogenalkyl, lower alkoxy, phenyl or phenoxy;
tetrahydronaphthyl;
$C_{3-7}$-cycloalkyl;
—$(CHR^3)_m$-phenyl, wherein m is 1, 2, or 3 and phenyl being unsubstituted or mono-, di-, or trisubstituted, independently, by lower alkyl, halogen,
lower halogenalkyl, lower alkoxy, phenyl or phenoxy and wherein
$R^3$ is independently selected from hydrogen, lower alkyl or phenyl;
—$(CH_2)_n$-heteroaryl, wherein n is 1, 2 or 3;
—$(CH_2)_n$-heteroaryl, wherein n is 1, 2, 3 and heteroaryl is mono-, di-, or trisubstituted, independently, by lower alkyl, halogen, lower halogenalkyl or lower alkoxy;
—C(O)—$CH_2$-phenyl, with phenyl being unsubstituted or mono-, di, or trisubstituted, independently, by lower alkyl, halogen, lower halogenalkyl, lower alkoxy, phenyl or phenoxy;
—C(O)—$CH_2$-heteroaryl; and
—C(O)—$CH_2$-heteroaryl, wherein heteroaryl is mono-, di, or trisubstituted, independently, by lower alkyl, halogen, lower halogenalkyl, or lower alkoxy; and
$R^2$ is selected from the group consisting of
lower alkyl, lower halogenalkyl;
phenyl, unsubstituted or mono-, di-, or trisubstituted, independently,
by lower alkyl, halogen, lower halogenalkyl, or lower alkoxy;
naphthyl, unsubstituted or mono-, di-, or trisubstituted, independently, by lower alkyl, halogen, lower halogenalkyl, or lower alkoxy;
heteroaryl, unsubstituted or mono-, di-, or trisubstituted, independently, by lower alkyl, lower halogenalkyl, or lower alkoxy;
—COOH;
—C(O)—$NR^4R^5$; wherein $R^4$ and $R^5$ are lower alkyl or together with the nitrogen atom to which they are attached form a 4-, 5- or 6-membered heterocycle which may contain a further heteroatom selected from O, N or S, and pharmaceutically acceptable salts thereof.

In preferred compounds of the present invention, $R^1$ is selected from the group consisting of
phenyl, unsubstituted or mono-, di-, or trisubstituted, independently, by lower alkyl, halogen,
lower halogenalkyl, lower alkoxy, phenyl or phenoxy;
naphthyl, unsubstituted or mono-, di-, or trisubstituted, independently, by lower alkyl, halogen, lower halogenalkyl, lower alkoxy, phenyl or phenoxy;
—$(CHR^3)_m$-phenyl, wherein m is 1 or 2 and with phenyl being unsubstituted or mono-, di, or trisubstituted, independently, by lower alkyl, halogen, lower halogenalkyl, lower alkoxy, phenyl or phenoxy and wherein $R^3$ is hydrogen;
—$(CH_2)_n$-heteroaryl, wherein n is 1 or 2;
—$(CH_2)_n$-heteroaryl, wherein n is 1 or 2 and with heteroaryl mono-, di, or trisubstituted, independently, by lower alkyl, halogen, lower halogenalkyl, or lower alkoxy;
—C(O)—$CH_2$-phenyl, with phenyl being unsubstituted or mono-, di, or trisubstituted, independently, by lower alkyl, halogen, lower halogenalkyl, lower alkoxy, phenyl or phenoxy;
—C(O)—$CH_2$-heteroaryl; and
—C(O)—$CH_2$-heteroaryl, with heteroaryl mono-, di-, or trisubstituted, independently, by lower alkyl, halogen, lower halogenalkyl, or lower alkoxy.

One group of preferred compounds of formula I according to the present invention are those compounds, wherein $R^1$ is selected from the group consisting of
phenyl, unsubstituted or mono-, di-, or trisubstituted, independently, by lower alkyl, halogen, lower halogenalkyl, lower alkoxy, phenyl or phenoxy;
naphthyl, unsubstituted or mono-, di-, or trisubstituted, independently, by lower alkyl, halogen, lower halogenalkyl, lower alkoxy, phenyl or phenoxy; and
—$(CHR^3)_m$-phenyl, wherein m is 1 or 2 and with phenyl being unsubstituted or mono-, di, or trisubstituted by lower alkoxy and wherein
$R^3$ is hydrogen.

Especially preferred are compounds of formula I, wherein $R^1$ is phenyl mono-, di-, or trisubstituted, independently, by lower alkyl, halogen, lower halogenalkyl, lower alkoxy, phenyl or phenoxy.

More preferably $R^1$ is phenyl di- or trisubstituted by lower alkoxy, with $R^1$ being 3,4-dimethoxyphenyl or 2,3,4-trimethoxyphenyl being most preferred.

A further group of preferred compounds of formula I are those, wherein $R^1$ is
—$(CH_2)_n$-heteroaryl, wherein n is 1 or 2; or
—$(CH_2)_n$-heteroaryl, wherein n is 1 or 2 and with heteroaryl mono-, di, or trisubstituted, independently, by lower alkyl, halogen, lower halogenalkyl, or lower alkoxy.

Preferred heteroaryl is indolyl or pyridyl.
Preferred meaning of n is 2.
Also preferred are compounds of formula I, wherein $R^1$ is
—C(O)—$CH_2$-phenyl, with phenyl being unsubstituted or mono-, di, or trisubstituted, independently, by lower alkyl, halogen, lower halogenalkyl, lower alkoxy, phenyl or phenoxy; or —C(O)—$CH_2$-heteroaryl.

Especially preferred are —C(O)—$CH_2$-phenyl and C(O)—$CH_2$-thienyl.

In preferred compounds of the present invention, $R^2$ is selected from the group consisting of lower alkyl;

phenyl, unsubstituted or mono-, di-, or trisubstituted, independently, by lower alkyl, halogen, lower halogenalkyl, or lower alkoxy;

heteroaryl, unsubstituted or mono-, di, or trisubstituted, independently, by lower alkyl, halogen, lower halogenalkyl, or lower alkoxy; and —C(O)—NR$^4$R$^5$, wherein R$^4$ and R$^5$ together with the nitrogen atom to which they are attached form a 5-membered heterocycle which may contain a further heteroatom selected from O, N or S.

Especially preferred are compounds of formula I, wherein $R^2$ is lower alkyl, with n-butyl being most preferred.

Another group of preferred compounds of formula I are those, wherein $R^2$ is phenyl, unsubstituted or mono-, di-, or trisubstituted, independently, by lower alkyl, halogen, lower halogenalkyl, or lower alkoxy.

Especially preferred are those compounds of formula I, wherein $R^2$ is phenyl or phenyl mono-, di-, or trisubstituted, independently, by lower alkyl or halogen.

Also preferred are compounds of formula I, wherein $R^2$ is heteroaryl, unsubstituted or mono-, di, or trisubstituted, independently, by lower alkyl, halogen, lower halogenalkyl, or lower alkoxy, with compounds, wherein heteroaryl is pyridyl or thienyl being especially preferred.

Further preferred are compounds of formula I, wherein $R^2$ is

—C(O)—NR$^4$R$^5$, wherein R$^4$ and R$^5$ together with the nitrogen atom to which they are attached form a 5-membered heterocycle which may contain a further heteroatom selected from O, N or S.

Especially preferred are compounds of formula I, wherein $R^2$ is

—C(O)-thiazolidinyl or —C(O)-dihydropyrrolyl.

Examples of compounds of the formula I of the present invention are the following:

(cis)-3-butyl-1-phenethyl-piperidine-4-yl-amine,
(trans)-3-butyl-1-phenethyl-piperidine-4-yl-amine,
(cis)-3-butyl-1-benzyl-piperidine-4-yl-amine
(trans)-3-butyl-1-benzyl-piperidine-4-yl-amine
(cis)-3-butyl-1-[2-(1H-indol-3-yl)-ethyl]-piperidine-4-ylamine, (
(trans)-3-butyl-1-[2-(1H-indol-3-yl)-ethyl]-piperidine-4-ylamine, (cis)-3-butyl-1-[2-(3,4-dimethoxy-phenyl-1yl)-ethyl]piperidine-4-ylamine,
(trans)-3-butyl-1-[2-(3,4-dimethoxy-phenyl-1yl)-ethyl]piperidine-4-ylamine,
(cis)-3-butyl-1-(3,4,5-trimethoxy-phenyl)-piperidine-4-yl-amine hydrochloride,
(trans)-3-butyl-1-(3,4,5-trimethoxy-phenyl)-piperidine-4-yl-amine hydrochloride,
(cis)-3-butyl-1-(4-phenoxy-phenyl)-piperidine-4-yl-amine,
(trans)-3-butyl-1-(4-phenoxy-phenyl)-piperidine-4-yl-amine,
(cis/trans)-3-butyl-1-(5,6,7,8-tetrahydro-naphthalen-1yl)-piperidine-4-yl-amine hydrochloride,
(cis)-3-butyl-1-(3,4-dimethoxy-phenyl)-piperidine-4-yl-amine hydrochloride,
(trans)-3-butyl-1-(3,4-dimethoxy-phenyl)-piperidine-4-yl-amine hydrochloride,
(cis)-3-butyl-1-naphthalen-2-yl-piperidine-4-yl-amine hydrochloride,
(trans)-3-butyl-1-naphthalen-2-yl-piperidine-4-yl-amine hydrochloride,
(cis/trans)-3-butyl-1-naphthalen-1-yl-piperidine-4-yl-amine hydrochloride,
(cis)-3-butyl-1-(3,4-dichloro-phenyl)-piperidine-4-yl-amine hydrochloride,
(cis)-3-butyl-1-(4-chloro-3-trifluoromethyl-phenyl)-piperidine-4-yl-amine hydrochloride,
(cis)-3-butyl-1-p-tolyl-piperidine-4-yl-amine hydrochloride,
(trans)-3-butyl-1-p-tolyl-piperidine-4-yl-amine hydrochloride,
(cis)-3-butyl-1-(3,5-dichloro-phenyl)-piperidine-4-yl-amine hydrochloride,
(cis/trans)-3-butyl-1-(3,5-dichloro-phenyl)-piperidine-4-yl-amine hydrochloride,
(cis)-3-butyl-4-methyl-1-phenyl-piperidine-4-yl-amine hydrochloride,
(trans)-3-butyl-4-methyl-1-phenyl-piperidine-4-yl-amine hydrochloride,
(cis)-3-butyl-1-(3-methoxy-5-trifluoromethyl-phenyl)-piperidine-4-yl-amine hydrochloride,
(cis/trans)-3-butyl-1-(3-methoxy-5-trifluoromethyl-phenyl)-piperidine-4-yl-amine hydrochloride,
(cis/trans)-3-butyl-1-cyclohexyl-piperidine-4-yl-amine hydrochloride,
(cis/trans)-3-butyl-1-(3,5-bis-trifluoromethyl-phenyl)-piperidine-4-yl-amine hydrochloride,
(cis)-3-butyl-1-(6-methoxy-biphenyl-3-yl)-piperidine-4-yl-amine hydrochloride,
(trans)-3-butyl-1-(6-methoxy-biphenyl-3-yl)-piperidine-4-yl-amine hydrochloride,
(cis/trans)-3-butyl-1-benzhydryl-4-yl-piperidine-4-yl-amine hydrochloride,
(cis)-3-phenyl-1-phenethyl-piperidine-4-yl-amine,
(trans)-3-phenyl-1-phenethyl-piperidine-4-yl-amine,
(cis)-3-phenyl-1-benzyl-piperidine-4-yl-amine,
(trans)-3-phenyl-1-benzyl-piperidine-4-yl-amine,
(cis/trans)-methyl-1'-phenethyl-1',2',3',4',5',6'-hexahydro-[2,3']bipyridinyl-4'-yl-amine,
(cis)-3-(3-chloro-phenyl)-1-phenethyl-piperidine-4-yl-amine,
(cis/trans)-3-(3-chloro-phenyl)-1-benzyl-piperidine-4-yl-amine,
(cis/trans)-3-(3-methyl-phenyl)-1-benzyl-piperidine-4-yl-amine,
(cis)-3-(3-chloro-phenyl)-1-[2-(3,4-dimethoxy-phenyl)-ethyl]-piperidine-4-yl-amine,
(trans)-1-benzyl-3-thiophen-2-yl-piperidine-4-yl amine
(cis)-3-o-tolyl-1-(3, 4, 5-trimethoxy-phenyl)-piperidine-4-yl-amine hydrochloride,
(trans)-3-o-tolyl-1-(3, 4, 5-trimethoxy-phenyl)-piperidine-4-yl-amine hydrochloride,
(cis/trans)-3-o-tolyl-1-(3, 4, 5-trimethoxy-phenyl)-piperidine-4-yl-amine hydrochloride,
(cis/trans)-1-(3,4-dimethoxy-phenyl)-3-m-tolyl-piperidine-4-yl-amine hydrochloride,
(cis/trans)-1-(3,4-dimethoxy-phenyl)-3-p-tolyl-piperidine-4-yl-amine hydrochloride,
(cis/trans)-1-(3,4-dimethoxy-phenyl)-3-(3,4-dimethyl-phenyl)-piperidine-4-yl-amine hydrochloride,
(cis/trans)-1-(3,4-dimethoxy-phenyl)-3-(3-methoxy-phenyl)-piperidine-4-yl-amine hydrochloride,
(cis/trans)-1'-(3,4-dimethoxy-phenyl)-1',2',3',4',5',6'-hexahydro-[2,3']bipyridinyl-4'-yl-amine,
((3R,4S)-4-amino-1-phenethyl-piperidine-3-yl)-thiazolidine-3-yl-methanone,
((3S,4R)-4-amino-1-phenethyl-piperidine-3-yl)-thiazolidine-3-yl-methanone,

[(3S,4R)-4-amino-1-(2-pyridin-2-yl-ethyl)-piperidine-3-yl]-thiazolidine-3-yl-methanone,
1-[(3S, 4R)-4-amino-3-(thiazolidine-3-carbonyl)-piperidine-1-yl]-2-phenyl-ethanone,
1-[(3S-4R)-4-amino-3-(thiazolidine-3-carbonyl)-piperidine-1-yl]-2-thiophen-2-yl-ethanone,
3-[(3S,4R) and (3R,4S)-4-amino-1-[2(3,4-dimethoxy-phenyl)-ethyl]-piperidine-3-carboxylic acid,
3-[(3S,4S) and (3R,4R)-4-amino-1-(3,4-dimethoxy-phenyl)-piperidine-3-yl]-thiazolidin-3-yl-methanone
3-[(3S,4S) and (3R,4R)-4-amino-1-(3,4-dimethoxy-phenyl)-piperidine-3-yl]-(2,5-dihydropyrrol-1-yl)-3-yl-methanone,
3-[(3S,4R) and (3R,4S)-4-amino-1-(3,4-dimethoxy-phenyl)-piperidine-3-yl]-(2,5-dihydropyrrol-1-yl)-3-yl-methanone, and pharmaceutically acceptable salts thereof.

Preferred compounds of formula I are selected from:
(cis)-3-butyl-1-phenethyl-piperidine-4-yl-amine,
(cis)-3-butyl-1-[2-(1H-indol-3-yl)-ethyl]-piperidine-4-ylamine,
(cis)-3-butyl-1-(3,4,5-trimethoxy-phenyl)-piperidine-4-yl-amine hydrochloride,
(cis)-3-butyl-1-(4-phenoxy-phenyl)-piperidine-4-yl-amine,
(cis)-3-butyl-1-(3,4-dimethoxy-phenyl)-piperidine-4-yl-amine hydrochloride,
(cis)-3-butyl-1-naphthalen-2-yl-piperidine-4-yl-amine hydrochloride,
(trans)-3-butyl-1-naphthalen-2-yl-piperidine-4-yl-amine hydrochloride,
(cis/trans)-3-butyl-1-naphthalen-1-yl-piperidine-4-yl-amine hydrochloride,
(cis)-3-butyl-1-(3,4-dichloro-phenyl)-piperidine-4-yl-amine hydrochloride,
(cis)-3-butyl-1-(4-chloro-3-trifluoromethyl-phenyl)-piperidine-4-yl-amine hydrochloride,
(cis)-3-butyl-1-p-tolyl-piperidine-4-yl-amine hydrochloride,
(cis)-3-butyl-1-(3,5-dichloro-phenyl)-piperidine-4-yl-amine hydrochloride,
(cis/trans)-3-butyl-1-(3,5-dichloro-phenyl)-piperidine-4-yl-amine hydrochloride,
(cis)-3-butyl-4-methyl-1-phenyl-piperidine-4-yl-amine hydrochloride,
(cis)-3-butyl-1-(3-methoxy-5-trifluoromethyl-phenyl)-piperidine-4-yl-amine hydrochloride,
(cis/trans)-3-butyl-1-(3-methoxy-5-trifluoromethyl-phenyl)-piperidine-4-yl-amine hydrochloride,
(cis)-3-butyl-1-(6-methoxy-biphenyl-3-yl)-piperidine-4-yl-amine hydrochloride,
(cis)-3-phenyl-1-phenethyl-piperidine-4-yl-amine,
(cis/trans)-methyl-1'-phenethyl-1',2',3',4',5',6'-hexahydro-[2,3' ]bipyridinyl-4'-yl-amine,
(cis)-3-(3-chloro-phenyl)-1-phenethyl-piperidine-4-yl-amine,
(cis/trans)-3-(3-chloro-phenyl)-1-benzyl-piperidine-4-yl-amine,
(cis/trans)-3-(3-methyl-phenyl)-1-benzyl-piperidine-4-yl-amine,
(cis)-3-(3-chloro-phenyl)-1-[2-(3,4-dimethoxy-phenyl)-ethyl]-piperidine-4-yl-amine,
(trans)-3-o-tolyl-1-(3, 4, 5-trimethoxy-phenyl)-piperidine-4-yl-amine hydrochloride,
(cis/trans)-3-o-tolyl-1-(3, 4, 5-trimethoxy-phenyl)-piperidine-4-yl-amine hydrochloride,
(cis/trans)-1-(3,4-dimethoxy-phenyl)-3-m-tolyl-piperidine-4-yl-amine hydrochloride,
(cis/trans)-1'-(3,4-dimethoxy-phenyl)-1',2',3',4',5',6'-hexahydro-[2,3']bipyridinyl-4'-yl-amine,
((3R,4S)-4-amino-1-phenethyl-piperidine-3-yl)-thiazolidine-3-yl-methanone,
((3S,4R)-4-amino-1-phenethyl-piperidine-3-yl)-thiazolidine-3-yl-methanone,
[(3S,4R)-4-amino-1-(2-pyridin-2-yl-ethyl)-piperidine-3-yl]-thiazolidine-3-yl-methanone,
1-[(3S,4R)-4-amino-3-(thiazolidine-3-carbonyl)-piperidine-1-yl]-2-phenyl-ethanone,
1-[(3S,4R)-4-amino-3-(thiazolidine-3-carbonyl)-piperidine-1-yl]-2-thiophen-2-yl-ethanone,
3-[(3S,4S) and (3R,4R)-4-amino-1-(3,4-dimethoxy-phenyl)-piperidine-3-yl]-thiazolidin-3-yl-methanone
3-[(3S,4S) and (3R,4R)-4-amino-1-(3,4-dimethoxy-phenyl)-piperidine-3-yl]-(2,5-dihydropyrrol-1-yl)-3-yl-methanone,
3-[(3S,4R) and (3R,4S)-4-amino-1-(3,4-dimethoxy-phenyl)-piperidine-3-yl]-(2,5-dihydropyrrol-1-yl)-3-yl-methanone, and pharmaceutically acceptable salts thereof.

Most preferred compounds are selected from
3-(3-chloro-phenyl)-1-phenethyl-piperidine-4-yl-amine,
3-(3-chloro-phenyl)-1-benzyl-piperidine-4-ylamine,
3-(3-chloro-phenyl)-1-[2-(3,4-dimethoxy-phenyl)-ethyl]-piperidine-4-ylamine,
1-(3,4-dimethoxy-phenyl)-3-m-tolyl-piperidine-4-yl amine hydrochlorid,
((3S,4R)-4-amino-1-phenethyl-piperidine-3-yl)-thiazolidine-3-yl-methanone,
[(3S,4R)-4-amino-1-(2-pyridin-2-yl-ethyl)-piperidine-3-yl]-thiazolidine-3-yl-methanone,
3-[(3S,4R) and (3R,4S)-4-amino-1-(3,4-dimethoxy-phenyl)-piperidine-3-yl]-thiazolidine-3-yl-methanone,
3-[(3S,4S) and (3R,4R)-4-amino-1-(3,4-dimethoxy-phenyl)-piperidine-3-yl]-thiazolidine-3-yl-methanone, and pharmaceutically acceptable salts thereof.

The compounds of formula I have two asymmetric carbon atoms and can exist in the form of optically pure enantiomers, mixtures of diastereomers, racemates, or mixtures of diasteroisomeric racemates. The invention embraces all of these forms.

In a preferred embodiment, $R^2$ and the amino group of the piperidine structure are in trans-configuration, i.e.

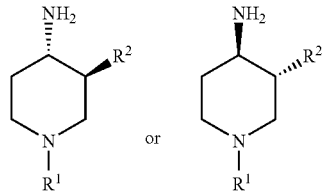

In a further preferable embodiment, $R^2$ and the amino group of the piperidine structure are in cis-configuration, i.e.

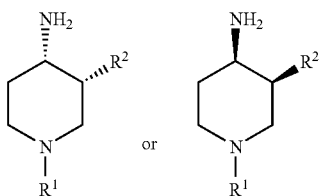

In a further embodiment the invention comprises a process for the manufacture of compounds of formula I, which process comprises
either
converting a compound of the formula

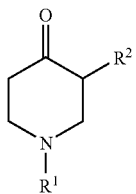

II wherein $R^1$ and $R^2$ are as defined before,
with hydroxylamine or a salt thereof into an oxime of the formula

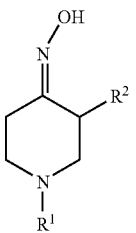

III wherein $R^1$ and $R^2$ are as defined before,
and further reducing the oxime of formula III by catalytic hydrogenation or alternatively by a reduction with a metal hydride into the compound of formula I or
deprotecting an 4-aminopiperidine derivative of the formula

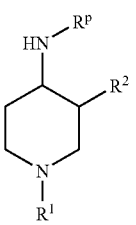

IV wherein $R^1$ and $R^2$ are as defined before and $R^P$ is an amino protecting group.
$R^P$ is a suitable amino protecting group such as benzyloxycarbonyl (Z or Cbz), allyloxycarbonyl (Aloc), 9-fluorenylmethoxycarbonyl (Fmoc), and preferably, tert-butoxycarbonyl (Boc).

In more detail, the compounds of formula I can be manufactured by the methods given below, by the methods shown in the examples or by analogous methods. Appropriate reaction conditions for the individual reaction steps are known to the person skilled in the art. Starting materials are commercially available or can be prepared by methods analogous to the method given below or in the examples or by methods known in the art.

The compounds of formula I of the present invention can be prepared as indicated in schemes 1 to 6 below:

4-Aminopiperidines of the formula I with $R^1$ having the meaning of —$(CHR^3)_m$-phenyl and —$(CH_2)_n$-heteroaryl, wherein $R^3$, n and m are as defined above and $R^2$ being lower alkyl can be prepared following scheme 1:

Scheme 1

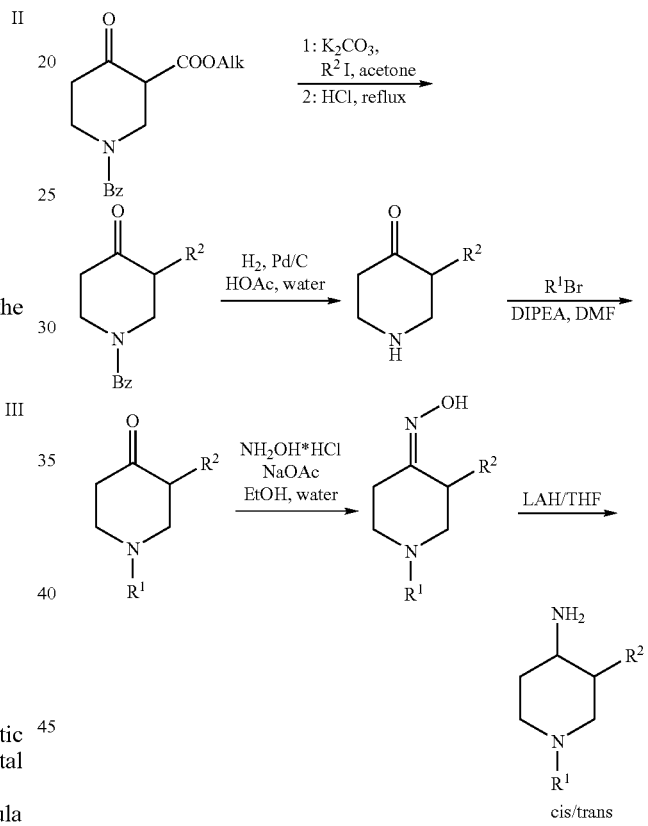

In a first step, $R^2$ with the meaning of lower alkyl is inserted in 3-position via a transformation of a N-protected 4-oxo-piperidine carboxylic acid alkyl ester (Alk=lower alkyl) with a suitable alkyl iodide. N-protection can easily be achieved with a benzyl group (Bz). In a second step, the N-protection is removed e.g. by a catalytic hydrogenation, and subsequently in a third step, an $R^1$-halogenide with $R^1$ having the meaning of —$(CHR^3)_m$-phenyl and —$(CH_2)_n$-heteroaryl is reacted with the deprotected piperidine to the respective 3-alkyl-1-aryl-4-oxo-piperidine. In case $R^1$ is benzyl, these two last steps can be omitted. Transformation of the 3-alkyl-1-aryl-4-oxo-piperidine into the desired 4-aminopiperidine can then take place via an oxime formation with hydroxylamine followed by a reduction for example by LiAlH$_4$ (LAH) in a suitable solvent.

4-Aminopiperidines of the formula I with $R^1$ having the meaning of unsubstituted or mono-, di, or trisubstituted phenyl, unsubstituted or mono-, di, or trisubstituted naphthyl, tetrahydronaphthyl or $C_{3-7}$-cycloalkyl and $R^2$ being lower alkyl can be prepared following scheme 2:

Scheme 2

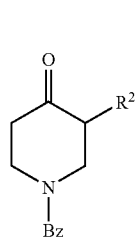 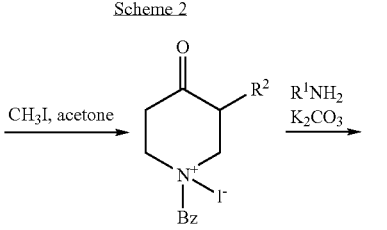

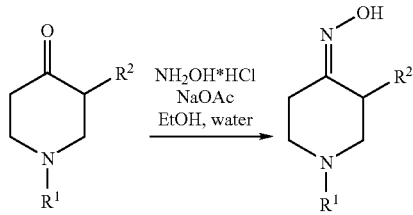

In a first step, a 4-oxo-piperidinium iodide can be formed from a suitably N-benzyl protected 3-alkyl-4-oxo-piperidine per reaction with methyl iodide in a suitable solvent. $R^1$ can be inserted by reaction of the 4-oxo-piperidinium iodide with the respective aniline $R^1NH_2$ thereby forming the respective 3-alkyl-1-aryl-4-oxo-piperidine. Transformation of this intermediate into the desired 4-aminopiperidine can then take place via an oxime formation with hydroxylamine followed by a reduction for example by catalytic hydrogenation in the presence of a common hydrogenation catalyst such as Raney Nickel or palladium/charcoal in a suitable solvent.

4-Aminopiperidines of the formula I with $R^1$ having the meaning of —$(CHR^3)_m$-phenyl and —$(CH_2)_n$-heteroaryl, wherein $R^3$, n and m are as above and $R^2$ being unsubstituted or mono-, di, or trisubstituted phenyl, unsubstituted or mono-, di, or trisubstituted naphthyl or unsubstituted or mono-, di, or trisubstituted heteroaryl can be prepared following scheme 3:

Scheme 3

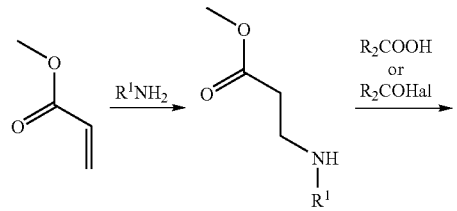

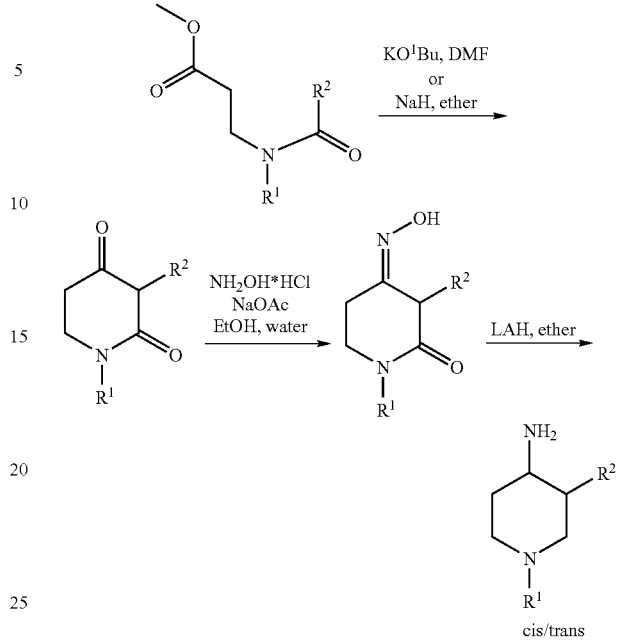

In a first reaction sequence an acrylic acid ester is reacted with the respective arylalkylamine $R^1NH_2$ to form the respective arylalkylamino propionic acid ester which is then converted with the respective arylacetic acid or aryl acetic acid halogenide $R^2COOH$ or $R^2COHal$ into an $R^2$ acetyl amino propionic acid ester. Subsequent ring formation with e.g. an alkalibutylate or with sodium hydride leads to a piperidine-2,4-dione which is then transformed with hydroxylamine to the piperidine-2,4dione-4-oxime. This intermediate can finally be reduced for example with $LiAlH_4$ (LAH) in a suitable solvent to the desired 4-aminopiperidine.

4-aminopiperidines of the formula I with $R^1$ having the meaning of unsubstituted or mono-, di, or trisubstituted phenyl, unsubstituted or mono-, di-, or trisubstituted naphthyl, tetrahydronaphthyl or $C_{3-7}$-cycloalkyl and $R^2$ being unsubstituted or mono-, di-, or trisubstituted phenyl, unsubstituted or mono-, di, or trisubstituted naphthyl or unsubstituted or mono-, di, or trisubstituted heteroaryl can be prepared following scheme 4:

Scheme 4

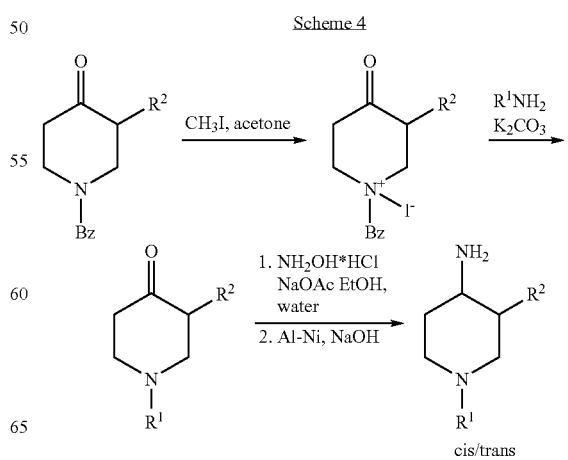

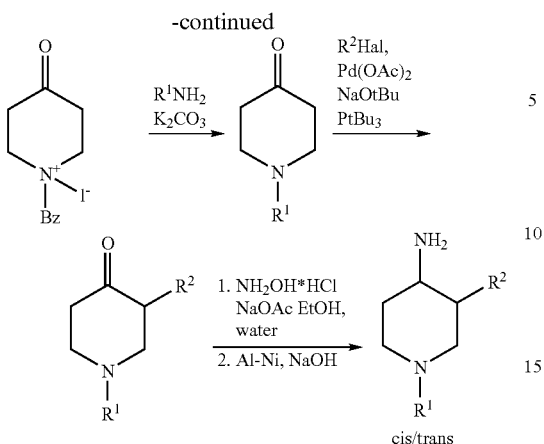

The synthesis of 1-aryl-3-aryl-4-amino piperidines can either be performed following scheme 2 via an N-benzyl-protected 3-aryl-4-oxo-piperidinium iodide which is treated with the aniline $R^1NH_2$ to give the respective 3-aryl-1-aryl-4-oxo-piperidine. Treatment of this compound with hydroxylamine will give the corresponding oxime that can be reduced subsequently to give the desired 4-amino-piperidine.

As an alternative an N-benzyl-protected 4-oxo-piperidinium iodide can be reacted in a first step with aryl aniline $R^1NH_2$ to give the 1-aryl-4-oxo-piperidine. The aryl-group in position 3 can then be introduced with an aryl halogenide $R^2Hal$ in the presence of Pd-acetate, sodium tert-butoxide and $P(tBu)_3$. The resulting 3-aryl-1-aryl-4-oxo-piperidine can then be transformed to the desired 4-amino piperidine as outlined above.

4-aminopiperidines of the formula I with $R^1$ having the meaning of $-(CHR^3)_m$-phenyl and $-(CH_2)_n$-heteroaryl, wherein $R^3$, n and m are as above and $R^2$ being $-C(O)-NR^4R^5$, wherein $R^4$ and $R^5$ are as above can be prepared following scheme 5:

Scheme 5

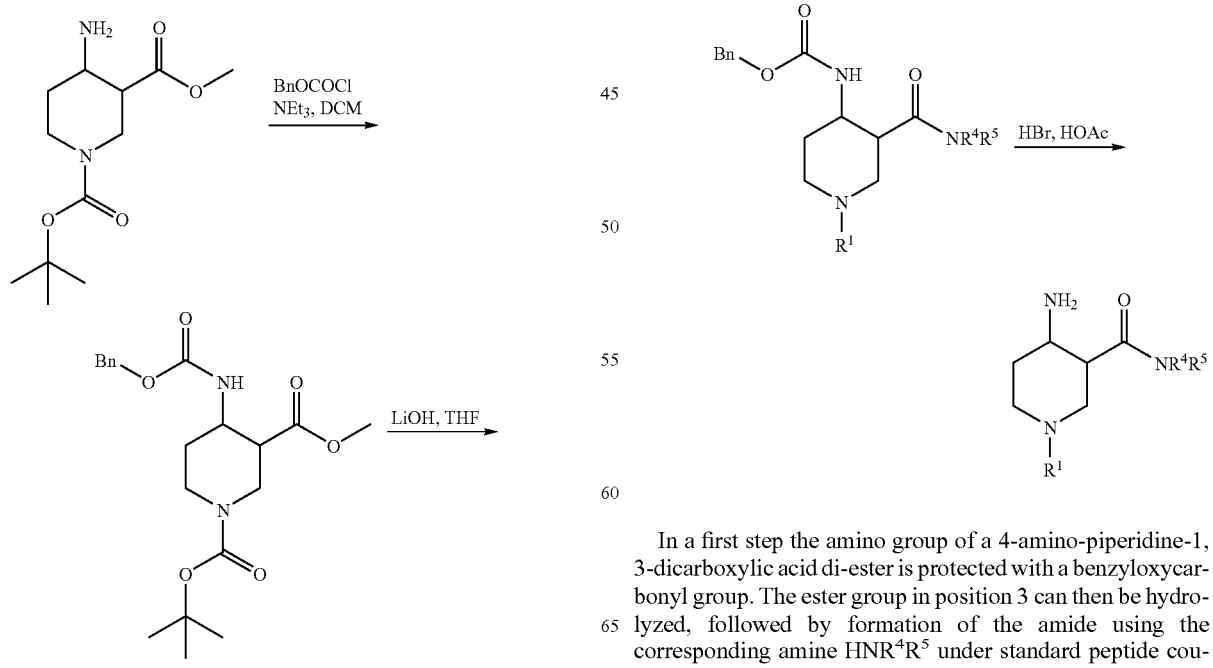

In a first step the amino group of a 4-amino-piperidine-1,3-dicarboxylic acid di-ester is protected with a benzyloxycarbonyl group. The ester group in position 3 can then be hydrolyzed, followed by formation of the amide using the corresponding amine $HNR^4R^5$ under standard peptide coupling conditions. In the subsequent steps, the BOC protecting group at position 1 can be removed for example by treatment with trifluoroacetic acid and then the arylakyl group can be introduced at N1 by treatment with the respective aryl alkyl halogenide $R^1$Hal. Finally the desired 4-aminopiperidine can be obtained by removal of the benzyloxycarbonyl protecting group in the presence of HBr.

4-aminopiperidines of the formula I with $R^1$ having the meaning of unsubstituted or mono-, di, or trisubstituted phenyl, unsubstituted or mono-, di-, or trisubstituted naphthyl, tetrahydronaphthyl or $C_{3-7}$-cycloalkyl and $R^2$ being unsubstituted or mono-, di, or trisubstituted phenyl, unsubstituted or mono-, di, or trisubstituted naphthyl or unsubstituted or mono-, di, or trisubstituted heteroaryl can be prepared following scheme 6:

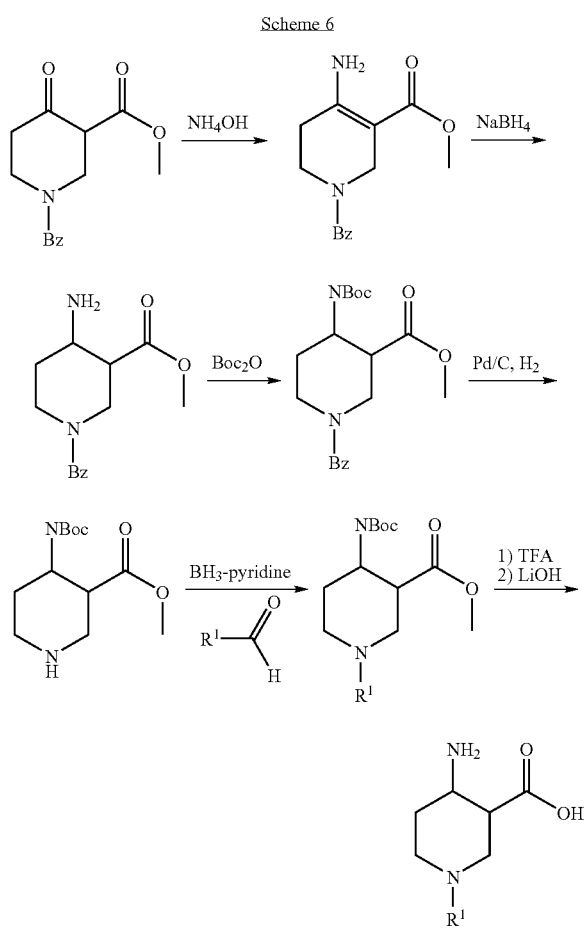

A 1-benzyl-4-oxo-piperidine-3-carboxylic acid ester is first reacted with ammonia to give the respective tetrahydropyridine which can then be reduced for example with sodium borohydride to give the 4-amino piperidine carboxylic acid ester. BOC protection of the amino group in 4-position and subsequent removal of the benzyl group by e.g. catalytic hydrogenation in the presence of a hydrogenation catalyst then affords 4-N-BOC protected piperidine-3-carboxylic acid ester. The arylalkyl group $R^1$ can be inserted using the respective aldehyde $R^1$CH=O followed by reduction. Removal of the BOC protecting group and ester hydrolysis with a suitable alkali hydroxide leads to the desired 1-arylalkyl-4-amino piperidine-3-carboxylic acid.

4-aminopiperidines of the formula I with $R^1$ having the meaning of —(CHR$^3$)$_m$-phenyl and —(CH$_2$)$_n$-heteroaryl, wherein $R^3$, n and m are as above and $R^2$ being —C(O)—NR$^4$R$^5$, wherein $R^4$ and $R^5$ are as above can be prepared following scheme 7:

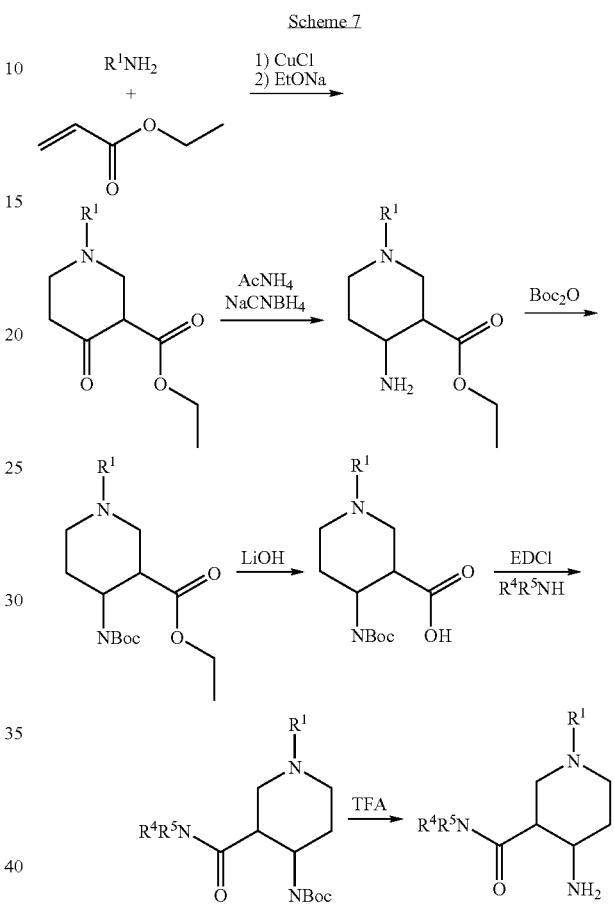

In a first reaction sequence an arylamine $R^1$ is reacted with an acrylic acid ester in the presence of CuCl and acetic acid to form the respective 1-aryl-4-oxo-piperidine-3-carboxylic acid ester. Treatment of this intermediate with ammonium acetate and sodium cyano borohydride gives the 1-aryl-4-amino piperidine-3-carboxylic acid ester. BOC protection of the free amino group in 4-position and subsequent ester hydrolysis provides the free carboxylic acid which can then used for coupling with amine $R^4R^5$NH. The desired 4-aminopiperidine can then be obtained by removal of the BOC protecting group with e.g. trifluoro acetic acid.

The invention further relates to compounds of formula I as defined above, when manufactured according to a process as defined above.

The invention also relates to compounds of formula I as defined above for use as therapeutic active substances for the treatment and/or prophylaxis of diseases which are associated with DPP-IV.

Such diseases which are associated with DPP-IV are diabetes, particularly non-insulin dependent diabetes mellitus, and/or impaired glucose tolerance, as well as other conditions wherein the amplification of action of a peptide normally inactivated by DPP-IV gives a therapeutic benefit.

In addition, the compounds of the present invention can also be used in the treatment and/or prophylaxis of obesity, metabolic syndrome, β-cell protection autoimmune diseases such as inflammatory bowel disease, encephalitis periaxialis scleroticans and rheumatoid arthritis, Colitis Ulcerrosa, Morbus Crohn, psoriasis, lichen planus and/or benign prostate hypertrophy. The compounds may also be useful for the prevention of AIDS (acquired immunodeficiency syndrome) or for the preventing metastasis, particularly preventing metastasis of breast and prostate cancer to lung. Furthermore, the compounds of the present invention can be used as diuretic agent and for the treatment and/or prophylaxis of hypertension.

As described above, the compounds of formula I of the present invention can be used as medicaments for the treatment and/or prophylaxis of such diseases which are associated with DPP-IV as defined above.

The invention therefore also relates to pharmaceutical compositions comprising a compound formula I of the present invention and a pharmaceutically acceptable carrier and/or adjuvant.

Further the invention relates to compounds of formula I of the present invention for use as therapeutic active substances, particularly as therapeutic active substances for the treatment and/or prophylaxis of the diseases which are associated with DPP-IV as defined above.

In another embodiment, the invention relates to a method for the treatment and/or prophylaxis of diseases which are associated with DPP-IV as defined above, which method comprises administering a compound of formula I to a human being or animal.

The invention further relates to the use of compounds formula I of the present invention for the treatment and/or prophylaxis of diseases which are associated with DPP-IV as defined above.

In context with the methods and uses defined above, the following diseases relate to a preferred embodiment: diabetes, particularly non-insulin dependent diabetes mellitus, impaired glucose tolerance, obesity, and/or metabolic syndrome or β-cell protection, preferably non-insulin dependent diabetes mellitus and/or impaired glucose tolerance.

The following tests were carried out in order to determine the activity of the compound of formula I.

Activity of DPP-IV inhibitors are tested with natural human DPP-IV derived from a human plasma pool or with recombinant human DPP-IV. Human citrate plasma from different donors is pooled, filtered through a 0.2 micron membrane under sterile conditions and aliquots of 1 ml are shock frozen and stored at −120° C. In the calorimetric DPP-IV assay 5 to 10 µl human plasma and in the fluorometric assay 1.0 µl of human plasma in a total assay volume of 100 µl is used as an enzyme source. The cDNA of the human DPP-IV sequence of amino acid 31- to 766, restricted for the N-terminus and the transmembrane domain, is cloned into *Pichia pastoris*. Human DPP-IV is expressed and purified from the culture medium using conventional column chromatography including size exclusion and anion and cation chromatography. The final enzyme preparation was observed on SDS-page stained with Coomassie blue and shown a purity of >95%. In the colorimetric DPP-IV assay 20 ng rec.h DPP-IV and in the fluorometric assay 2 ng rec-h DPP-IV in a total assay volume of 100 µl is used as enzyme source.

In the fluorogenic assay Ala-Pro-7-amido-4-trifluoromethylcoumarin (Calbiochem No 125510) is used as a substrate. A 20 mM stock solution in 10% DMF/H$_2$O is stored at −20° C. until use. In IC$_{50}$ determinations a final substrate concentration of 50 µM is used. In assays to determine kinetic parameters as K$_m$, V$_{max}$, K$_i$, the substrate concentration is varied between 10 µM and 500 µM.

In the colorimetric assay H-Ala-Pro-pNA.HCl (Bachem L-1115) is used as a substrate. A 10 mM stock solution in 10% MeOH/H$_2$O is stored at −20° C. until use. In IC$_{50}$ determinations a final substrate concentration of 200 µM is used. In assays to determine kinetic parameters as K$_m$, V$_{max}$, K$_i$, the substrate concentration is varied between 100 µM and 2000 µM.

Fluorescence is detected in a Perkin Elmer Luminescence Spectrometer LS 50B at an excitation wavelength of 400 nm and an emission wavelength of 505 nm continuously every 15 seconds for 10 to 30 minutes. Initial rate constants are calculated by best fit linear regression.

The absorption of pNA liberated from the colorimetric substrate is detected in a Packard Spectra Count at 405 nm continuously every 2 minutes for 30 to 120 minutes. Initial rate constants are calculated by best fit linear regression.

DPP-IV activity assays are performed in 96 well plates at 37° C. in a total assay volume of 100 µl. The assay buffer consists of 50 mM Tris/HCl pH 7.8 containing 0.1 mg/ml BSA and 100 mM NaCl. Test compounds are solved in 100% DMSO, diluted to the desired concentration in 10% DMSO/H$_2$O concentration in the assay is 1% (v/v). At this concentration enzyme inactivation by DMSO is <5%. Compounds are with (10 minutes at 37° C.) and without pre-incubation with the enzyme. Enzyme reactions are started with substrate application followed by immediate mixing.

IC$_{50}$ determinations of test compounds are calculated by non-linear best fit regression of the DPP-IV inhibition of at least 5 different compound concentrations. Kinetic parameters of the enzyme reaction are calculated at least 5 different substrate concentrations and at least 5 different test compound concentrations.

The compounds of the present invention exhibit IC$_{50}$ values of 0.1 µM to 100 µM, more preferably of 0.1 µM to 10 µM, as shown in the following table:

| Example | IC$_{50}$ [µM] |
|---|---|
| 23 | 0.16 |
| 29 | 0.59 |
| 36 | 0.29 |
| 40 | 0.82 |

The compound of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to an person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following Examples serve to illustrate the present invention in more detail. They are, however, not intended to limit its scope in any manner.

EXAMPLES

Abbreviations Used:
DCM: dichloromethane; HOAc: acetic acid; AcOEt: ethyl acetate; DMF: dimethylformamide; DIPEA: diisopropylethylamine (Huenig's base); THF: tetrahydrofuran; LAH: lithium aluminium hydride; CDI: carbonyldiimidazole; TFA: trifluoro acetic acid; EDCl: N-(3-dimethylaminopropyl)-N'-ethylcarbodiimide HCl; HOBt: 1-hydroxybenzotriazole. RT: room temperature; HV: high vacuum. TLC: thin layer chromatography.

Example 1

3-Butyl-1-phenethyl-piperidine-4-yl-amine

Step A]: 1-Benzyl-3-butyl-piperidine-4-one

To a suspension of anhydrous potassium carbonate (22.8 g) and 1-benzyl-4-oxo-piperidine-3-carboxylic acid ethyl ester (10 g) in acetone (125 ml) was added a solution of butyl iodide (13.4 g, 8.3 ml) in acetone (50 ml) under argon over a period of 30 minutes. The resulting suspension was stirred at RT for 30 min and then refluxed for 12 hours. The suspension was cooled, filtered and concentrated in vacuo. The residue was dissolved in DCM and the solution was washed with water and brine, dried over $Na_2SO_4$ and evaporated. To the residue was added aqueous HCl (20%, 100 ml) and the solution was refluxed for 24 hours. The solution was evaporated and the residue was dissolved in DCM, washed with 10% aq. $Na_2CO_3$ solution and brine, dried and evaporated. The crude product was purified by flash chromatography (ethyl acetate/hexanes 1:2) to give the product as a slightly yellow oil (6.4 g). MS (ESI): 246.4 ($MH^+$).

Step B]: 3-Butyl-piperidine-4-one

To a solution of 1-benzyl-3-butyl-piperidine-4-one (1.3 g) in HOAc/water 3:1 (25 ml) was added 10% Pd on charcoal (130 mg). A hydrogen atmosphere was introduced by repeated evacuation/gas introduction. The suspension was vigorously stirred for 5 hours. The catalyst was removed by filtration through dicalite and the filtrate was concentrated in vacuo. The oily residue was treated with 10% aq. $Na_2CO_3$ and then extracted into DCM. The organic layer was separated, dried over $Na_2SO_4$, filtered and evaporated to give the crude product as slightly yellow oil (680 mg) which was used without further purification. MS (ESI): 156.2 ($MH^+$).

Step C]: 3-Butyl-1-phenethyl-piperidine-4-one

To a solution of 3-Butyl-piperidine-4-one (250 mg) in DMF (5 ml) was added DIPEA (468 mg) and then a solution of (2-bromoethyl)-benzene (373 mg) in DMF (5 ml) over a period of 45 min. The resulting mixture was stirred at RT for 1 hour and then heated to 60° C. for 6 hours. The reaction mixture was cooled, diluted with ether and the organic solution was washed with 10% aq. $Na_2CO_3$ solution twice and brine. The organic layer was dried over $MgSO_4$, filtered and evaporated to give a residue which was purified by flash chromatography (ethyl acetate/hexanes 1:3) to give the product as a colorless liquid (355 mg). MS (ESI): 260.4 ($MH^+$).

Step D]: 3-Butyl-1-phenethyl-piperidine-4-one oxime

3-Butyl-1-phenethyl-piperidine-4-one (300 mg), NaOAc (878 mg) and hydroxylamine hydrochloride (708 mg) were suspended in ethanol/water (1:1, 10 ml) and the mixture was heated to reflux for 5 hours. The clear solution that resulted from this treatment was cooled, diluted with water and basified with 10% aq. $Na_2CO_3$ to pH 10. The suspension was extracted with DCM and the organic layer was washed with brine, dried ($MgSO_4$) and evaporated. The product was sufficiently pure for the next step. Yellowish glass, mixture of cis and trans diastereomers (332 mg). MS (ESI): 261.4 ($MH^+$).

Step E] 3-Butyl-1-phenethyl-piperidine-4-ylamine

3-Butyl-1-phenethyl-piperidine-4-one oxime (218 mg) was dissolved in THF (10 ml) and LAH (261 mg) was added in one portion. The suspension was then allowed to stir at RT for 24 hours. The reaction mixture was carefully pipetted onto 5% aq. $NaHCO_3$ solution and the aqueous layer was extracted with DCM. The organic layer was washed with brine, dried ($MgSO_4$) and evaporated to give a colorless oil. This was purified by flash chromatography (gradient of MeOH in DCM containing 1% $NH_4OH$) to give the product as cis and trans diastereomers (cis: 127 mg; trans: 36 mg). MS (ESI): 261.4 ($MH^+$).

Example 2

3-Butyl-1-benzyl-piperidine-4-yl-amine

This compound was synthesized in analogy to example 1, with the exception that Steps B] and C] were omitted altogether and the benzyl group was carried through the whole synthesis. Cis and trans diastereomers as colorless oils. MS (ESI): 247.4 (MH$^+$).

Example 3

3-Butyl-1-[2-(1H-indol-3-yl)-ethyl]-piperidine-4-ylamine

This compound was synthesized as described in example 1 from 1-benzyl-4-oxo-piperidine-3-carboxylic acid ethyl ester and 3-(2-bromo-ethyl)-1H-indole as the alkylating agent in Step C]. Cis and trans diastereomers as colorless oils. MS (ESI): 300.5 (MH$^+$).

Example 4

3-Butyl-1-[2-(3,4-dimethoxy-phenyl-1-yl)-ethyl]-piperidine-4-ylamine

This compound was synthesized as described in example 1 from 1-benzyl-4-oxo-piperidine-3-carboxylic acid ethyl ester and (2-bromoethyl)-3,4-dimethoxybenzene as the alkylating agent used in Step C]. Cis and trans diastereomers as colorless oils. MS (ESI): 321.4 (MH$^+$).

Example 5

3-Butyl-1-(3,4,5-trimethoxy-phenyl)-piperidine-4-yl-amine hydrochloride

Step A]: 1-Benzyl-3-butyl-1-methyl-4-oxo-piperidinium iodide

To a solution of 3-butyl-1-benzyl-piperidine-4-one (9080 mg) in acetone (40 ml) was slowly added methyl iodide (6303 mg) at room temperature. The solution was stirred at room temperature for three hours. A white solid precipitated and was filtered off. The solid was washed four times with 50 ml of acetone and dried under reduced pressure. The filtrate was evaporated and the residue was stirred with ethyl acetate. The white solid was filtered, washed with ethyl acetate and dried under vacuum. The two solids were combined to yield 1-benzyl-3-butyl-1-methyl-4-oxo-piperidinium iodide as a white powder (11200 mg). MS (ESI): 204.2 (M−1$^-$).

Step B]: 3-Butyl-1-(3,4,5-trimethoxy-phenyl)-piperidine-4-one

A slurry of 1-benzyl-3-butyl-1-methyl-4-oxo-piperidinium iodide (306 mg) in water (2 ml) was added in one portion to a refluxing solution of 3,4,5-trimethoxy aniline (929 mg) and anhydrous potassium carbonate (33 mg) in ethanol (4 ml). The dark solution was heated to reflux for three hours. Water was added and the reaction was extracted twice with DCM. The combined organic layers were dried over sodium sulfate, filtered and the solvent was evaporated to leave a dark oil, which was purified by flash chromatography (ethyl acetate/hexanes 1:1) to give the product as a colorless oil (520 mg). MS (ESI): 322.4 (MH$^+$).

Step C]: 3-Butyl-1-(3,4,5-trimethoxy-phenyl)-piperidine-4-yl-amine hydrochloride The ketone (460 mg) was dissolved in ethanol (60 ml). Hydroxylamine hydrochloride (109 mg) and sodium acetate (129 mg) were added and the solution was stirred at room temperature for one hour. After TLC control, Raney-Nickel was added (Nr 313 Degussa B1132) and the reaction was stirred at room temperature under an atmosphere of hydrogen over night. The catalyst was filtered off and the filtrate was concentrated. The residue was purified by chromatography on silica gel (DCM/MeOH/25% aqueous NH$_4$OH solution 95:5:1). The separated products were dissolved in ethanol and 1 ml of saturated ethanolic hydrogen chloride solution was added. The solutions were evaporated to yield the cis-(150 mg) and the trans-diastereomers (160 mg) as light yellow solids. MS (ESI): 323.4 (MH$^+$).

Example 6

3-Butyl-1-(4-phenoxy-phenyl)-piperidine-4-yl-amine hydrochloride

This compound was synthesized in analogy to example 5 using Steps B] and C] from 1-benzyl-3-butyl-1-methyl-4-oxo-piperidinium iodide and 4-phenoxy-aniline with the exception that Step C] was replaced by a different method.

Step C (modified version)]: 3-Butyl-1-(4-phenoxy-phenyl)-piperidine-4-yl-amine hydrochloride 3-Butyl-1-(4-phenoxy-phenyl)-piperidine-4-one (320 mg) was dissolved in ethanol (8 ml). Hydroxylamine hydrochloride (76 mg) and sodium acetate (89 mg) were added. The reaction turned yellow and the solution was stirred at room temperature for two hours. TLC control indicated the formation of the E/Z-oximes. Water (8 ml) was added. A suspension was obtained to which Al—Ni-alloy (300 mg) was added. 32% aqueous sodium hydroxide solution (1.4 ml) was added slowly. The reaction turned warm. After complete addition, the reaction was stirred for two hours at room temperature and the solid was filtered off. The precipitate was washed with DCM. The aqueous solution was extracted with DCM. The combined organic layers were washed with brine, dried over sodium sulfate, filtered and the solvent was evaporated. The residue was purified by flash chromatography (DCM/MeOH/aq. sat. NH$_4$OH solution 100:5:1).

The separated products were dissolved in ethanol and 1 ml of saturated ethanolic hydrogen chloride solution was added. The solutions were evaporated to yield the cis-(117 mg) and the trans-diastereomer (52 mg) as light yellow solids. MS (ESI): 325.5 (MH$^+$) trans and cis.

Example 7

3-Butyl-1-(5,6,7,8-tetrahydro-naphthalen-1-yl)-piperidine-4-yl-amine hydrochloride The compound was synthesized in analogy to example 6 from 1-benzyl-3-butyl-1-methyl-4-oxo-piperidinium iodide and 5-amino-tetraline to yield a mixture of cis- and trans-diastereomers as a white solid. Separation of the diastereomers (as the free amines) using flash chromatography was not possible. MS (ESI): 287.3 (MH$^+$).

Example 8

3-Butyl-1-(3,4-dimethoxy-phenyl)-piperidine-4-yl-amine hydrochloride

This compound was synthesized in analogy to example 6 from 1-benzyl-3-butyl-1-methyl-4-oxo-piperidinium iodide and 3,4-dimethoxy-aniline to yield the cis- and the trans-diastereomers as white solids. MS (ESI): 293.4 (MH$^+$) cis- and trans-diastereomer.

Example 9

3-Butyl-1-naphthalen-2-yl-piperidine-4-yl-amine hydrochloride

This compound was synthesized in analogy to example 6 from 1-benzyl-3-butyl-1-methyl-4-oxo-piperidinium iodide and 2-naphthyl-amine to yield a 5/2-mixture of the cis- and trans-diastereomers and the pure trans-diastereomer as white solids. MS (ESI): 283.2 (MH$^+$) cis- and trans-diastereomer.

Example 10

3-Butyl-1-naphthalen-1-yl-piperidine-4-yl-amine hydrochloride

The compound was synthesized in analogy to example 6 from 1-benzyl-3-butyl-1-methyl-4-oxo-piperidinium iodide and 1-naphthylamine to yield a 1/2-mixture of the cis/trans-diastereomers as a white solid. Separation of the diastereomers (as the free amines) using flash chromatography was not possible. MS (ESI): 283.2 (MH$^+$).

Example 11

3-Butyl-1-(3,4-dichloro-phenyl)-piperidine-4-yl-amine hydrochloride

The compound was synthesized in analogy to example 6 from 1-benzyl-3-butyl-1-methyl-4-oxo-piperidinium iodide and 3,4-dichloro-aniline to yield the cis-diastereomer as a white solid. MS (ESI): 301.3 (MH$^+$).

Example 12

3-Butyl-1-(4-chloro-3-trifluoromethyl-phenyl)-piperidine-4-yl-amine hydrochloride This compound was synthesized in analogy to example 6 from 1-benzyl-3-butyl-1-methyl-4-oxo-piperidinium iodide and 4-chloro-3-trifluoromethyl-aniline to yield the cis-diastereomer and a 1/1-mixture of the cis- and trans-diastereomers as white solids. MS (ESI): 335.3 (MH$^+$) cis- and trans-diastereomer.

Example 13

3-Butyl-1-p-tolyl-piperidine-4-yl-amine hydrochloride

This compound was synthesized in analogy to example 6 from 1-benzyl-3-butyl-1-methyl-4-oxo-piperidinium iodide and 4-methyl-aniline to yield the cis- and trans-diastereomers as white solids. MS (ESI): 247.4 (MH$^+$).

Example 14

3-Butyl-1-(3,5-dichloro-phenyl)-piperidine-4-yl-amine hydrochloride and 3-butyl-1-phenyl-piperidine-4-yl-amine hydrochloride This compound was synthesized in analogy to example 6 from 1-benzyl-3-butyl-1-methyl-4-oxo-piperidinium iodide and 3,5-dichloro-4-methyl-aniline to yield the cis- and a 1/1-mixture of the cis- and trans-diastereomers as white solids. MS (ESI): 301.3 (MH$^+$).

Overreduction led to the formation of the dehalogenated cis- and trans-phenyl derivatives, which were separated as the amines during flash chromatography. The hydrochlorides of the cis- and trans-diastereomers were isolated as white solids. MS (ESI): 233.3 (MH$^+$).

Example 15

3-Butyl-1-(3-methoxy-5-trifluoromethyl-phenyl)-piperidine-4-yl-amine hydrochloride This compound was synthesized in analogy to example 6 from 1-benzyl-3-butyl-1-methyl-4-oxo-piperidinium iodide and 3-methoxy-5-trifluoromethyl-aniline to yield a mixture of cis- and trans-diastereomers and the cis-diastereomer as white solids. MS (ESI): 331.4 (MH$^+$).

Example 16

3-Butyl-1-cyclohexyl-piperidine-4-yl-amine hydrochloride

This compound was synthesized in analogy to example 6 from 1-benzyl-3-butyl-1-methyl-4-oxo-piperidinium iodide and cyclohexyl amine to yield a mixture of cis- and trans-diastereomers as a white solid. $^1$H NMR (DMSO): δ 2.81-2.65 (m, 2H), 2.60-2.00 (m, 5H), 1.74-1.60 (m, 5H), 1.60-1.40 (m, 3H), 1.40-1.00 (10H), 0.87 (t, 3H).

Example 17

1-(3,5-Bis-trifluoromethyl-phenyl)-3-butyl-piperidine-4-yl-amine hydrochloride

The compound was synthesized in analogy to example 6 from 1-benzyl-3-butyl-1-methyl-4-oxo-piperidinium iodide and 3,5-bis(trifluoromethyl)-aniline to yield a mixture of cis- and trans-diastereomers as a white solid. MS (ESI): 369.3 (MH$^+$).

Example 18

3-Butyl-1-(6-methoxy-biphenyl-3-yl)-piperidine-4-yl-amine hydrochloride

This compound was synthesized in analogy to example 6 from 1-benzyl-3-butyl-1-methyl-4-oxo-piperidinium iodide and 6-methoxy-biphenyl-3-ylamine to yield the cis- and the trans-diastereomers as white solids. $^1$H NMR (DMSO, cis-diastereomer): δ 7.47 (d, 2H), 7.38 (t, 2H), 7.32 (t, 1H), 6.97 (d, 1H), 6.89 (d, 1H), 6.82 (s, 1H), 3.67 (s, 3H), 3.07 (dd, 2H), 2.98 (m, 2H), 2.86 (dd, 1H), 1.62 (m, 3H), 1.29 (m, 6H), 0.88 (t, 3H). $^1$H NMR (DMSO, trans-diastereomer): δ 7.47-7.20 (m, 8H), 3.62 (s, 3H), 3.54 (br d, 2H), 2.64 (m, 2H), 2.36 (m, 1H), 1.79 (m, 3H), 1.33 (m, 6H), 0.88 (t, 3H).

Example 19

Benzhydryl-3-butyl-piperidine-4-yl-amine hydrochloride

The compound was synthesized in analogy to example 6 from (rac)-1-benzyl-3-butyl-1-methyl-4-oxo-piperidinium iodide and diphenyl methyl amine to yield a 1/1-mixture of cis/trans-diastereomers as a white solid. $^1$H NMR (DMSO): δ 7.37 (m, 4H), 7.27 (m, 4H), 7.16 (t, 2H), 4.26 & 4.22 (2s, 1H), 2.81-2.73 (m, 3H), 2.48-2.08 (m, 3H), 1.56-1.05 (m, 8H), 0.84 & 0.77 (2t, 3H).

Example 20

Phenyl-1-phenethyl-piperidine-4-yl-amine]

Step A]: 3-Phenethylamino-propionic acid ethyl ester

Phenylethyl amine (10 g) was dissolved in EtOH (50 ml) and then treated with acrylic acid ethyl ester (8.3 g) dropwise under argon at RT. The resulting mixture was allowed to stir over night and was evaporated and dried in vacuo. The residue (18.9 g) was used without further purification. Colorless liquid, MS (ESI): 222.3 (MH$^+$).

Step B]: 3-(Phenethyl-phenylacetyl-amino)-propionic acid ethyl ester

Phenethylamino-propionic acid ethyl ester (8.0 g) was dissolved in absolute pyridine (12 ml) and cooled to 0° C. by means of an ice bath. Phenylacetic acid chloride (1.5 ml) was then added dropwise over a period of 10 min; a yellow suspension was obtained. The mixture was then heated to 60° C. for 2.5 hours, cooled to RT and then allowed to stir over night. The mixture was poured into ice/water containing 25% HCl and the aqueous layer was extracted with ethyl acetate. The organic layer was separated, washed with brine, dried over Na$_2$SO$_4$ and evaporated. The residue was purified by flash chromatography (ethyl acetate/hexanes 1:4) to give the product as a yellow oil (3.9 g). MS (ESI): 340.4 (MH$^+$).

Step C]: 1-Phenethyl-3-phenyl-piperidine-2,4-dione

Sodium hydride (1.1 g, 50% in mineral oil) was suspended in ether (40 ml) under argon at RT. 3-(Phenethyl-phenylacetyl-amino)-propionic acid ethyl ester (2.5 g) was added in portions followed by addition of abs. EtOH (0.5 ml). The resulting mixture was refluxed for 2 hours, cooled and poured into water/ice/1 N HCl. The aqueous layer was extracted with ethyl acetate and the organic layer was separated, washed with brine, dried over Na$_2$SO$_4$, filtered and evaporated. The residue was purified by flash chromatography (ethyl acetate/hexanes 1:1 and then DCM/MeOH 95:5) to give the desired product as a light yellow foam (801 mg). MS (ESI: 294.4 (MH$^+$).

Step D]: 1-Phenethyl-3-phenyl-piperidine-2,4-dione 4-oxime

Phenethyl-3-phenyl-piperidine-2,4-dione (781 mg), sodium acetate (1.15 g) and hydroxylamine hydrochloride (925 mg) were suspended in EtOH/water 1:1 (25 ml) and the mixture was refluxed for 4 hours. The mixture was then poured into ice/water/1N NaOH and extracted with ethyl acetate. The organic layer was washed with brine, dried and evaporated to give the crude product that was purified by flash chromatography (DCM/MeOH/NH$_4$OH 98:2:0.25) to give the compound as a white foam (489 mg). MS (ESI): 309.4 (MH$^+$).

Step E]: 1-Phenethyl-3-phenyl-piperidine-4-yl amine

Phenethyl-3-phenyl-piperidine-2,4-dione 4-oxime (480 mg) was dissolved in abs. ether (30 ml) under argon. LAH (473 mg) was added in one portion and the resulting suspension was refluxed over night. The mixture was carefully poured into 1M aqueous sodium potassium tartrate solution and the aqueous layer was extracted with ethyl acetate. The organic layer was washed with brine, dried (Na$_2$SO$_4$), filtered and evaporated. The residue was purified by flash chromatography (gradient of MeOH in DCM containing 0.25% NH$_4$OH and then DCM/MeOH/NH$_4$OH 85/15/0.25) to give the compound as the cis diastereomer (95 mg) and trans diastereomer (101 mg) as colorless oils. MS (ESI): 281.4 (MH$^+$).

Example 21

Phenyl-1-benzyl-piperidine-4-yl-amine]

This compound was made according to example 20, Step B] to E] from 3-benzylamino-propionic acid ethyl ester and phenylacetic acid chloride. Cis and trans diastereomers as yellow oils. MS (ESI): 326.4 (MH$^+$).

Example 22

Methyl-1'-phenethyl-1',2',3',4',5',6'-hexahydro-[2,3']bipyridinyl-4'-ylamine

This compound was made according to example 20, Step A] to E] from phenethylamine and ethyl acrylate but with a modified coupling step B] where (4-methyl-pyridin-2-yl)-acetic acid was used instead of the corresponding acid chloride.

Step A] (4-Methyl-pyridin-2-yl)-acetic acid (4-Methyl-pyridin-2-yl)-acetic acid ethyl ester (1.0 g)—prepared according to Chem. Parm. Bull 32 (12), 1984, 4866-4872—was dissolved in ethanol (30 ml) and treated with a 1M ethanolic NaOH solution (5.83 ml). The mixture was refluxed for 4 hours, cooled and evaporated in vacuo. The residue was dissolved in water (50 ml) and the pH was adjusted to 3.0 with 1M HCl. The solvent was evaporated and the residue was suspended in ethanol (150 ml) and filtered. The clear filtrate was evaporated to dryness and the residue was dried in vacuo to give a light yellow solid (1.0 g). NMR (DMSO-d$_6$): 8.65 (d, 1H); 7.72 (s, 1H), 7.68 (d, 1H), 4.04 (s, 2H), 2.49 (s, 3H).

Step B] 3-{[2-(4-Methyl-pyridin-2-yl)-acetyl]-phenethyl-amino}-propionic acid ethyl ester (4-Methyl-pyridin-2-yl)-acetic acid (1.0 g), carbonyldiimidazole (CDI, 1.07 g) and DIPEA (0.856 g) were added to THF (15 ml) and the light brown suspension was allowed to stir at RT for 1 hour. To the mixture was added 3-phenethylamino-propionic acid ethyl ester (0.898 g) dropwise and the resulting mixture was stirred at 55° over night. The mixture was poured into ice/water and the pH was adjusted to 5.0. The mixture was extracted with ethyl acetate and the organic layer was separated, washed with brine, dried over Na$_2$SO$_4$, filtered and evaporated. The residue was purified by flash chromatography (ethyl acetate/hexanes 2:1) to give the desired product as a light brown liquid (0.462 g). MS (ESI): 355.0 (MH$^+$).

The final product of this reaction sequence was obtained as a mixture of cis and trans diastereomers, yellow oil. MS (ESI): 296.4 (MH$^+$).

Example 23

3-(3-Chloro-phenyl)-1-phenethyl-piperidine-4-ylamine

This compound was made according to example 22 from phenethylamine, ethyl acrylate and (3-chloro-phenyl) acetic acid. The desired compound was obtained as the cis-diastereomer as a yellow oil. MS (ESI): 315.1 (MH+).

Example 24

3-(3-Chloro-phenyl)-1-benzyl-piperidine-4-ylamine

This compound was made according to example 20, steps B] to E] from 3-benzylamino-propionic acid ethyl ester and (3-chloro-phenyl) acetic acid chloride. The desired compound was obtained as a mixture of cis- and trans-diastereomer as a yellow oil. MS (ESI): 301.2 (MH+).

Example 25

3-(3-Methyl-phenyl)-1-benzyl-piperidine-4-ylamine

This compound was made according to example 20, steps B] to E] from 3-benzylamino-propionic acid ethyl ester and (3-methyl-phenyl) acetic acid chloride. The desired compound was obtained as a mixture of cis and trans-diastereomers as a yellow oil. MS (ESI): 281.3 (MH+).

Example 26

3-(3-Chloro-phenyl)-1-[2-(3,4-dimethoxy-phenyl)-ethyl]-piperidine-4-ylamine

This compound was made according to example 20 from ethyl acrylate, 2-(3,4-dimethoxy-phenyl)-ethylamine and (3-chloro-phenyl) acetic acid chloride. The desired compound was obtained as the cis-diastereomer as a yellow oil. MS (ESI): 375.2 (MH+).

Example 27

Benzyl-3-thiophen-2-yl-piperidine-4-ylamine

This compound was made in analogy to example 20, steps B] to E] from 3-benzylamino-propionic acid ethyl ester and thiophene-2-acetylchloride. The desired compound was obtained as the trans-diastereomer as a yellow oil. MS (ESI): 273.2 (M–H−).

Example 28

3-o-Tolyl-1-(3,4,5-trimethoxy-phenyl)-piperidine-4-yl-amine hydrochloride

Step A]: 1-Benzyl-1-methyl-4-oxo-3-o-tolyl-piperidinium iodide

To a solution of 1-benzyl-3-o-tolyl-piperidine-4-one (5165 mg) in acetone (25 ml) was slowly added methyl iodide (3048 mg) at room temperature. The solution was stirred at room temperature over night. A white solid precipitated and was filtered off. The solid was washed four times with 50 ml of acetone and dried under reduced vacuum. The filtrate was evaporated and the residue was stirred with ethyl acetate. The white solid was filtered, washed with ethyl acetate and dried under vacuum. The two solids were combined to yield 1-benzyl-3-butyl-1-methyl-4-oxo-piperidinium iodide as a yellowish solid (4400 mg). MS (ESI): 294.3 (M–I−).

Step B]: 3-o-Tolyl-1-(3,4,5-trimethoxy-phenyl)-piperidine-4-one

A slurry of 1-benzyl-1-methyl-4-oxo-3-o-tolyl-piperidinium iodide (1000 mg) in water (5 ml) was added in one portion to a refluxing solution of 3,4,5-trimethoxy aniline (395 mg) and anhydrous potassium carbonate (37 mg) in ethanol (10 ml). The reaction was heated to reflux over night. Water was added and the reaction was extracted four times with DCM. The combined organic layers were dried over sodium sulfate, filtered and the solvent was evaporated to leave a red-brown oil, which was purified by flash chromatography (diethyl ether) to give the product as a yellow oil (600 mg). MS (ESI): 356.2 (MH+).

Step C]: 3-o-Tolyl-1-(3,4,5-trimethoxy-phenyl)-piperidine-4-yl-amine hydrochloride 3-o-Tolyl-1-(3,4,5-trimethoxy-phenyl)-piperidine-4-one (300 mg) was dissolved in ethanol (8 ml). Hydroxylamine hydrochloride (64 mg) and sodium acetate (76 mg) were added. The solution turned from yellow to a brown suspension. After 3 hours stirring at room temperature water (8 ml) was added. A suspension was obtained to which Al—Ni-alloy (300 mg) was added. 32% aqueous sodium hydroxide solution (1.4 ml) was added slowly; warming of the reaction mixture was observed. After complete addition, the reaction was stirred for two days at room temperature and the solid was filtered off. The precipitate was washed with DCM. The aqueous solution was extracted with DCM. The combined organic layers were washed with brine, dried over sodium sulfate, filtered and the solvent was evaporated. The residue was purified by flash chromatography (DCM/MeOH/aq. sat MH solution 100:5:1). The separated products were dissolved in ethanol and 1 ml of saturated ethanolic hydrogen chloride solution was added. The solutions were evaporated to yield the cis-diastereomer (76 mg), a mixture of cis- and trans-diastereomers (170 mg) and the trans-diastereomer (40 mg) as white solids. MS (ESI): 357.3 (MH+).

Example 29

1-(3,4-Dimethoxy-phenyl)-3-m-tolyl-piperidine-4-yl amine hydrochloride

Step A]: 1-(3,4-Dimethoxy-phenyl)-piperidine-4-one

A slurry of 1-benzyl-1-methyl-4-oxo-piperidinium iodide (9270 mg), 3,4-dimethoxy aniline (3900 mg) and anhydrous potassium carbonate (437 mg) in ethanol (90 ml)/water (45 ml) were heated to reflux for 6 hours. Additional potassium carbonate (200 mg) was added and the reaction was heated to 100° C. over night. Water (50 ml) was added to the reaction mixture, which was extracted three times with DCM. The combined organic layers were washed with water and brine, dried over sodium sulfate, filtered and the solvent was evaporated in vacuo to leave the crude product as a dark oil. The residue was purified by column chromatography (ethyl acetate/hexanes=1:1) to yield the product as a yellow solid (3700 mg). MS (ESI): 236.1 (MH+).

Step B]: 1-(3,4-Dimethoxy-phenyl)-3-m-tolyl-piperidine-4-one

Palladium acetate (23.8 mg), sodium tert-butoxide (306 mg) and 1-(3,4-dimethoxy-phenyl)-piperidine-4-one were dissolved in oxygen free tetrahydrofuran (3 ml) under argon. The mixture was immediately degassed. After addition of 3-bromotoluene (363 mg) and tri(tert-butyl)phosphine (25.8 mg) the mixture was stirred at 50° C. over night. There was still some starting material left. The reaction was therefore heated to 70° C. for 2 hours. After cooling the mixture was diluted with ethyl acetate. It was washed with 1N aqueous hydrochloride solution, water and brine. The organic layer was dried over sodium sulfate, filtered and concentrated in Step C]: 1-(3,4-Dimethoxy-phenyl)-3-m-tolyl-piperidine-4-yl amine hydrochloride 1-(3,4-Dimethoxy-phenyl)-3-m-tolyl-piperidine-4-one (169 mg) was dissolved in ethanol (4 ml). Hydroxylamine hydrochloride (40 mg) and sodium acetate (47 mg) were added. The clear yellow solution turned to a suspension. After 3 hours stirring at room temperature water (4 ml) was added. A suspension was obtained to which Al—Ni-alloy (150 mg) was added. 32% aqueous sodium hydroxide solution (0.7 ml) was added slowly; warming of the reaction mixture was observed. After complete addition, the reaction was stirred for two days at room temperature and the solid was filtered off. The precipitate was washed with DCM. The aqueous solution was extracted with DCM. The combined organic layers were washed with brine, dried over sodium sulfate, filtered and the solvent was evaporated. The residue was purified by flash chromatography (DCM/MeOH/aq. sat $NH_3$ solution 100:5:1). The separated products were dissolved in ethanol and 1 ml of saturated ethanolic hydrogen chloride solution was added. The solutions were evaporated to yield the cis-diastereomer (15 mg), a mixture of the trans- and cis-diastereomers (144 mg) and the trans-diastereomer (6 mg) as white solids. MS (ESI): 327.3 ($MH^+$).

Example 30

1-(3,4-Dimethoxy-phenyl)-3-p-tolyl-piperidine-4-yl-amine hydrochloride

The compound was synthesized in analogy to example 29, steps B] and C] from 1-(3,4-dimethoxy-phenyl)-piperidine-4-one and 4-bromo-toluene to yield a mixture of cis- and trans-diastereomers as a white solid. In step B] the aryl bromide and tri(tert-butyl)phosphine were added as a solution in tetrahydrofuran and the reaction was run at 70° C. for 5 hours. Separation of the diastereomers (free bases) could not be achieved by flash chromatography. MS (ESI): 327.3 ($MH^+$).

Example 31

1-(3,4-Dimethoxy-phenyl)-3-(3,4-dimethyl-phenyl)-piperidine-4-yl amine hydrochloride The compound was synthesized in analogy to example 30 from 1-(3,4-dimethoxy-phenyl)-piperidine-4-one and 4-bromo-o-xylene to yield a mixture of cis/trans-diastereomers as a white solid. Separation of the diastereomers (free bases) could not be achieved by flash chromatography. MS (ESI): 341.3 ($MH^+$).

Example 32

1-(3,4-Dimethoxy-phenyl)-3-(3-methoxy-phenyl)-piperidine-4-yl-amine hydrochloride The compound was synthesized in analogy to example 30 from 1-(3,4-dimethoxy-phenyl)-piperidine-4-one and 4-bromo-anisole to yield a mixture of cis/trans-diastereomers as a white solid. Separation of the diastereomers (free bases) could not be achieved by flash chromatography. MS (ESI): 343.3 ($MH^+$).

Example 33

1'-(3,4-Dimethoxy-phenyl)-1',2',3',4',5',6'-hexahydro-[2,3']bipyridinyl-4'-ylamine The compound was synthesized in analogy to example 30 from 1-(3,4-dimethoxy-phenyl)-piperidine-4-one and 2-bromo-pyridine to yield a mixture of cis/trans-diastereomers as a white solid. Separation of the diastereomers could not be achieved by flash chromatography. MS (ESI): 314.3 ($MH^+$).

Example 34

((3R,4S)-4-Amino-1-phenethyl-piperidine-3-yl)-thiazolidin-3-yl-methanone

Step A]: (3R,4S)-4-Benzyloxycarbonylamino-piperidine-1,3-dicarboxylic acid 1-tert-butyl ester 3-methyl ester (3R,4S)-4-Amino-piperidine-1,3-dicarboxylic acid 1-tert-butyl ester 3-methyl ester (540 mg, synthesized according to Duan, Jingwu et al, PCT Int. Appl. (2001), WO 2001070673 A2) and WO 2002002525) was dissolved in abs. DCM and $NEt_3$ (0.39 ml) was added.

Benzylchloroformiate (0.33 ml) was added and the mixture was allowed to stir at RT over night. The reaction mixture was poured into ice/brine und the aqueous layer was extracted with ethyl acetate. The organic layer was washed with brine, dried and evaporated to give a residue that was purified by flash chromatography (gradient of ethyl acetate in heptane) to give a colorless gum (598 mg). MS (ESI): 393.2 ($MH^+$).

Step B]: (3R,4S)-4-Methoxycarbonylamino-piperidinee-1,3-dicarboxylic acid 1-tert-butyl ester (3R, 4S)-4-Benzyloxycarbonylamino-piperidine-1,3-dicarboxylic acid 1-tert-butyl ester 3-methyl ester (580 mg) was dissolved in THF (20 ml) and a 1 M aqueous solution of LiOH was added (3.0 ml). The mixture was allowed to stir at RT for 20 hours. The solution was poured into ice/brine containing 2 M HCl (2.5 ml). The aqueous layer was extracted with ethyl acetate and the organic layer was separated, washed with brine, dried ($Na_2SO_4$) and evaporated. The residue was dried in high vacuum to furnish a colorless foam (558 mg). MS (ESI): 377.3 ($MH^+$).

Step C]: (3R,4S)-4-Benzyloxycarbonylamino-3-(thiazolidine-3-carbonyl)-piperidine-1-carboxylic acid tert-butyl ester (3R,4S)-4-Methoxycarbonylamino-piperidine-1,3-dicarboxylic acid 1-tert-butyl ester (557 mg) was dissolved in abs. DCM (20 ml). To this solution were added subsequently benzotriazol-1-yloxy)-tripyrrolidinophosphonium-hexafluorophosphate (919 mg), triethylamine (0.47 ml) and—after 5 minutes—thiazolidine (151 mg). The mixture was allowed to stir for 5 hours at RT. The mixture was poured into ice/brine and the aqueous layer was extracted with ethyl acetate. The organic layer was washed with brine, dried ($Na_2SO_4$) and evaporated. The residue was purified by flash chromatography (gradient of ethyl acetate in heptane) to give the product as a white foam (403 mg). MS (ESI): 450.3 ($MH^+$).

Step D]: (3R,4S)-[3-(Thiazolidine-3-carbonyl)-piperidine-4-yl]-carbamic acid benzyl ester (3R, 4S)-4-Benzyloxycarbonylamino-3-(thiazolidine-3-carbonyl)-piperidine-1-carboxylic acid tert-butyl ester (325 mg) was dissolved in abs. DCM (12 ml) and TFA (0.44 ml) was added dropwise. The resulting mixture was then allowed to stir at RT over night and was then evaporated. The residue was transferred into ice/brine, basified to pH 10 with 2N NaOH and extracted with ethyl acetate. The organic layer was washed with brine, dried ($Na_2SO_4$) and evaporated to give a residue that was purified by flash chromatography to give the desired product as a white foam (260 mg). MS (ESI): 350.1 $MH^+$).

Step E]: (3R-4S) [1-Phenethyl-3-(thiazolidine-3-carbonyl)-piperidine-4-yl]-carbamic acid benzyl ester (3R,4S)-3-(Thiazolidine-3-carbonyl)-piperidine-4-yl]-carbamic acid benzyl ester (255 mg) was dissolved in DMF (5 ml) and DIPEA (0.28 ml) was added. After 20 minutes, a solution of 2-(bromoethyl)-benzene (169 mg) in DMF (4 ml) was added over a period of 15 minutes. The mixture was stirred at RT over night. The reaction mixture was poured into ice/water/sat. $Na_2CO_3$ solution and the aqueous layer was extracted with ethyl acetate. The organic layer was washed with brine, dried over $Na_2SO_4$ and evaporated. The residue was purified by flash chromatography to give the desired product as a light yellow oil (308 mg). MS (ESI): 454.2 ($MH^+$).

Step F]: (3R,4S)-(4-Amino-1-phenethyl-piperidine-3-yl)-thiazolidin-3-yl-methanone (3R,4S)-[1-Phenethyl-3-(thiazolidine-3-carbonyl)-piperidine-4-yl]-carbamic acid benzyl ester (216 mg) was treated with 33% HBr in acetic acid (2.5 ml) for 2 hours at RT under argon. Ether (15 ml) was added and the resulting suspension was cooled to −10° C. and stirred for 1 hour. The solvent was then decanted and the solid washed with a small amount of EtOH. The residue was then dissolved in water (pH was adjusted to 10 with conc. $NH_4OH$) and the aqueous layer was saturated with NaCl and extracted with ethyl acetate. The organic layer was separated, washed with brine, dried ($Na_2SO_4$) and evaporated to give a residue that was purified by flash chromatography (gradient of MeOH in DCM containing 0.5% $NH_4OH$) to furnish the desired product as a light yellow oil (92 mg). MS (ESI): 320.1 $MH^+$).

Example 35

((3S, 4R)-4-Amino-1-phenethyl-piperidine-3-yl)-thiazolidin-3-yl-methanone

This material was obtained as described in example 34 from the opposite enantiomer (3S, 4R)-4-amino-piperidine-1,3-dicarboxylic acid 1-tert-butyl ester 3-methyl ester, thiazolidine and 2-(bromoethyl)-benzene. Yellow oil. MS (ESI): 320.4 ($MH^+$).

Example 36

[((3S, 4R)-4-Amino-1-(2-pyridin-2-yl-ethyl)-piperidine-3-yl]-thiazolidin-3-yl-methanone This material was obtained as described in example 34 from the opposite enantiomer (3S, 4R)-4-amino-piperidine-1,3-dicarboxylic acid 1-tert-butyl ester 3-methyl ester, thiazolidine and 2-(2-bromo-ethyl)-pyridine (synthesized according to *Synthesis*, 5, 1987, 452-455). Yellow oil. MS (ESI): 321.4 ($MH^+$).

Example 37

1-[(3S, 4R)-4-Amino-3-(thiazolidine-3-carbonyl)-piperidine-1-yl]-2-phenyl-ethanone]

This material was obtained according to example 34, but with modified Steps E] and F]:

Step E]: [1-Phenylacetyl-3-(thiazolidine-3-carbonyl)-piperidine-4-yl]-carbamic acid methyl ester 3-(Thiazolidine-3-carbonyl)-piperidine-4-yl]-carbamic acid benzyl ester (250 mg) was dissolved in abs. DCM (8 ml) and DIPEA (0.184 ml) was added. The mixture was allowed to stir at −15° C. (ice/salt bath) for 20 min and then phenylacetylchlorid (0.104 ml) was added dropwise. The mixture was warmed to 0° C. and stirred for 30 min. The reaction mixture was poured into ice/water/sat. $NaHCO_3$ solution and extracted with ethyl acetate. The organic layer was separated, washed with brine, dried over $Na_2SO_4$ and evaporated in vacuo. The residue was purified by flash chromatography to give the desired product [1-phenylacetyl-3-(thiazolidine-3-carbonyl)-piperidine-4-yl]-carbamic acid methyl ester (304 mg) as a white foam. MS (ESI): 468.1 ($MH^+$).

Step F]: 1-[(3S, 4R)-4-Amino-3-(thiazolidine-3-carbonyl)-piperidine-1-yl]-2-phenyl-ethanone The reaction was performed as described in example 34, Step F] from [1-phenylacetyl-3-(thiazolidine-3-carbonyl)-piperidine-4-yl]-carbamic acid methyl ester (295 mg) and HBr in HOAc (3 ml) but with a modified purification step: The product was purified by preparative HPLC (RPC18, gradient of $CH_3CN$ in water containing 0.05% formic acid). The appropriate fractions were evaporated to give the desired product as the formic acid salt as a white solid (12 mg). MS (ESI): 334.4 ($MH^+$, free base).

Example 38

1-[(3S-4R)-4-Amino-3-(thiazolidine-3-carbonyl)-piperidine-1-yl]-2-thiophen-2-yl-ethanone This material was obtained according to example 37 with the appropriate reagents: Colorless gum: MS (ESI): 340.4 ($MH^+$, free base).

Example 39

3 [(3S,4R) and (3R,4S)-4-Amino-1-(3,4-dimethoxy-phenyl)-piperidine-3-yl]-thiazolidin-3-yl-methanone Step A]: 4-Amino-1-benzyl-1,2,5,6-tetrahydro-pyridine-3-carboxylic acid methyl ester rac-1-Benzyl-4-oxo-piperidine-3-carboxylic acid methyl ester (25 g) was suspended in 100 ml ammonium hydroxide 25% and heated at 50° C. during 18 h. The mixture was cooled with ice and then, $NaBH_4$ (1 g) was added in several portions. Stirring was continued for 18 h at ambient temperature and the mixture was diluted with water/ice, with cooling, and extracted with AcOEt. The organic extract was washed with brine and dried over sodium sulfate. Removal of the solvent under reduced pressure gave a brown oil which was purified by column chromatography (silica gel, heptane/AcOEt, 1/1) and precipitated (AcOEt/heptane) to give 12.1 g (56%) of the title compound as white solid and 6 g (25%) of the title compound as its borane salt.

Amino-1-benzyl-1,2,5,6-tetrahydro-pyridine-3-carboxylic acid methyl ester: MS: 247.2 $(M+H)^+$ NMR: (DMSO, 1H, 400 MHz, δ, TMS): 2.28 (t, 2H), 2.46 (t, 2H), 2.99 (s, 2H), 3.49 (s, 3H), 3.53 (s, 2H), 7.22-7.34 (m, 5H), 6.90 and 7.80 (2 s. large, 2H).

Amino-1-benzyl-1,2,5,6-tetrahydro-pyridine-3-carboxylic acid methyl ester; BH$_3$ salt: MS: 247.2 (M+H)$^+$ NMR: (DMSO, 1H, 400 MHz, δ, TMS) 2.45-2.60 (m, 2H), 2.80-2.90 (m, 1H), 2.92-3.02 (m, 1H), 3.30-3.45 (2d, 2H), 3.53 (s, 3H), 3.80-4.00 (2d, 2H), 7.31-7.40 (m, 5H), 6.90 and 7.80 (2 s. large, 2H).

Step B]: rac-4-Amino-1-benzyl-piperidine-3-carboxylic acid ethyl ester

Amino-1-benzyl-1,2,5,6-tetrahydro-pyridine-3-carboxylic acid methyl ester BH$_3$ salt was heated in ethanol with NaOH 25%. After 72 h at 50° C. the mixture was cooled, washed with water/ice and extracted with AcOEt. The extract was washed with brine and dried over sodium sulfate. Removal of the solvent under reduced pressure gave an yellow oil. To a suspension of 4-amino-1-benzyl-1,2,5,6-tetrahydro-pyridine-3-carboxylic acid methyl ester (21 g) in 200 ml THF was added 50 ml TFA at 10° C. under an argon atmosphere. After stirring for 15 min at 0° C., NaBH$_4$ (6.43 g) was added over a period of 75 min at 10° C. The mixture was stirred for additional 90 min at 0° C. After adding 100 ml NH$_4$Cl saturated, the solution was extracted two times with CH$_2$Cl$_2$. The combined extracts were washed with water/ice and brine and dried over sodium sulfate. Evaporation of the solvent gave a yellow oil of the title compound which was taken for the next step without purification Step C]: (3S,4R) and (3R,4S)-1-Benzyl-4-tert-butoxycarbonylamino-piperidine-3-carboxylic acid ethyl ester and (3S,4S) and (3R,4R)-1-Benzyl-4-tert-butoxycarbonylamino-piperidine-3-carboxylic acid ethyl ester Rac-4-Amino-1-benzyl-piperidine-3-carboxylic acid ethyl ester (80.7 mMol, 21 g) and BOC$_2$O (20.5 g) in 200 ml CH$_2$Cl$_2$ were stirred 17 h at ambient temperature. The solution was evaporated and chromatographied (silica gel, AcOEt/heptane, 1/1) to give 7.05 g of the racemic trans isomer, 1.88 g of the racemic cis isomer and 13.87 g of the racemic mixture of the diastereomers. (3S,4R) and (3R,4S)-1-Benzyl-4-tert-butoxycarbonylamino-piperidine-3-carboxylic acid ethyl ester: MS: 363.3 (M+H)$^+$ NMR: (DMSO, 1H, 400 MHz, δ, TMS) 1.11 (t, 3H), 1.36 (s, 9H), 1.65-1.71 (m, 2H), 2.30-2.37 (m, 2H), 2.49-2.55 (m, 1H), 2.63-2.80 (m, 2H), 3.38 (d, 1H), 3.51 (d, 1H), 3.80-3.92 (m, 1H), 4.02 (q, 2H), 6.60 (s large, 1H), 7.21-7.32 (m, 5H). S,4S) and (3R,4R)-1-Benzyl-4-tert-butoxycarbonylamino-piperidine-3-carboxylic acid ethyl ester: MS: 363.3 (M+H)$^+$ NMR: (DMSO, 1H, 400 MHz, δ, TMS) 1.13 (t, 3H), 1.35 (s, 9H), 1.40-1.50 (m, 1H), 1.62-1.71 (m, 1H), 1.97-2.11 (m, 2H), 2.43-2.50 (m, 2H), 2.74-2.83 (m, 2H), 3.45 (s, 2H), 3.95-4.04 (m, 2H), 6.85 (d, 1H), 7.22-7.33 (m, 5H).

Step D]: (3R,4R) and (3S,4S)-4-tert-Butoxycarbonylamino-1-[2-(3,4-dimethoxy-phenyl)-ethyl]-piperidine-3-carboxylic acid ethyl ester A suspension of (3S,4S) and (3R,4R)-1-benzyl-4-tert-butoxycarbonylamino-piperidine-3-carboxylic acid ethyl ester (700 mg) and 200 mg of Pd/C (10%) in 10 ml of EtOH and 1 ml of Hunig's base was hydrogenated at 22° C./1 bar overnight. The suspension was filtered, the filtrate evaporated and the residue purified by column chromatography (silica gel, AcOEt) to give a pale yellow solid (538 mg). To a solution of the above product (272 mg) and 3,4-dimethoxybenzeneacetaldehyde (CAS 5703-21-9, 191 mg) in ethanol at 0° C., was added a solution 8M of pyridine-borane-complex (0.5 ml). After 2 h stirring at 0° C. and 3 h at ambient temperature, the mixture was diluted with water/ice and extracted twice with ethyl acetate. The combined organic layers were washed with brine and dried over sodium sulfate. Removal of the solvent under reduced pressure gave an oil which was purified by column chromatography (silica gel, AcOEt) to give 196 mg (45%) of the title compound as an yellow oil. MS: 437.4 (M+H)$^+$ NMR: (DMSO, 1H, 400 MHz, δ, TMS) 1.14-1.23 (m, 3H), 1.36 (s, 9H), 1.40-1.52 (m, 1H), 1.65-1.71 (m, 1H), 2.02 (ddd, 1H), 2.12 (ddd. 1H), 2.42-2.50 (m, 2H), 2.58-2.69 (m, 2H), 2.85 (d, 1H), 2.98 (d, 1H), 3.45-3.57 (m, 1H), 3.62-3.72 (m, 1H), 3.70 (s, 3H), 3.72 (s, 3H), 4.02 (q, 2H), 6.70 (dd, 1H), 6.81-6.86 (m, 3H).

Step E]: (3R,4R) and (3S,4S)-4-Amino-1-[2-(3,4-dimethoxy-phenyl)-ethyl]-piperidine-3-carboxylic acid ethyl ester A solution of (3R,4R) and (3S,4S)-4-tert-butoxycarbonylamino-1-[2-(3,4-dimethoxy-phenyl)-ethyl]-piperidine-3-carboxylic acid ethyl ester (24 mg) in 1 ml TFA was stirred 1 h at 0° C. The mixture was poured onto NaOH 1M/ice and extracted with AcOEt. The combined organic layers were washed with brine and dried over sodium sulfate. Removal of the solvent under reduced pressure gave an oil which was purified by column chromatography (Isolute SPE Flash NH$_2$ 10 g, AcOEt/heptane, 1/2) to give 9 mg (50%) of the title compound. MS: 337.4 (M+H)$^+$ Step F]: (3R,4R) and (3S,4S)-4-Amino-1-[2-(3,4-dimethoxy-phenyl)-ethyl]-piperidine-3-carboxylic acid (3R,4R) and (3S,4S)-4-Amino-1-[2-(3,4-dimethoxy-phenyl)-ethyl]-piperidine-3-carboxylic acid ethyl ester (262 mg) and lithium hydroxide (166 mg) in 5 ml THF, 5 ml MeOH and 1 ml H$_2$O were stirred for 24 h at ambient temperature. The mixture was diluted with buffer pH 7 and extracted with AcOEt. The combined organic layers were washed with brine and dried over sodium sulfate. Removal of the solvent under reduced pressure gave an oil which was purified by column chromatography (Isolute SPE Flash NH$_2$, AcOEt) and precipitated (AcOEt/heptane) to give 90 mg (37%) of the title compound as a white solid. MS: 309.2 (M+H)$^+$ NMR: (DMSO, 1H, 400 MHz, δ, TMS) 1.92-2.02 (m, 1H), 2.10-2.20 (m, 1H), 2.75-3.10 (2m, 6H), 3.35-3.48 (m, 2H), 3.55-3.62 (m, 1H), 3.70-3.80 (m, 1H), 3.71 (s, 3H), 3.75 (s, 3H), 6.76 (dd, 1H), 6.85-6.90 (m, 2H), 8.3-8.7 (s.broad, 3H).

Example 40

3 [(3S,4R) and (3R,4S)-4-Amino-1-(3,4-dimethoxy-phenyl)-piperidine-3-yl]-thiazolidin-3-yl-methanone Step A]: rac-1-(3,4-Dimethoxy-phenyl)-4-oxo-piperidine-3-carboxylic acid ethyl ester A mixture of 3,4-dimethoxyaniline (12 g), copper (I) chloride (1.7 g), acetic acid (9 ml) and ethyl acrylic acid (26 ml) was heated 17 hours at 140° C., cooled with ice, diluted with CH$_2$Cl$_2$ and washed successively with water, ammonium hydroxide 10%, water and brine. The organic layers were dried over MgSO$_4$, filtered and evaporated. Chromatography (silica gel, AcOEt/heptane, 1/1) delivered a yellow oil (22.8 g) which was dissolved in 50 ml xylene and sodium ethoxide (4.42 g) was added. Then, the suspension was stirred 2 h at 140° C., cooled, diluted with AcOEt and washed with water and brine. The aqueous phases were extracted twice with AcOEt, the organic layers were dried over MgSO$_4$, filtered, evaporated and chromatographied (silica gel, AcOEt/heptane, 1/3) to obtain the title compound as a white solid (13.53 g, 68%). MS: 308.2 (M+H)$^+$ Step B]: rac-4-Amino-1-(3,4-dimethoxy-phenyl)-piperidine-3-carboxylic acid ethyl ester A suspension of rac-1-(3,4-dimethoxy-phenyl)-4-oxo-piperidine-3-carboxylic acid ethyl ester (640 mg) and ammonium acetate (3 g) in 10 ml methanol was stirred 18 h at RT., then sodium cyanoborohydride (2 g) was added. After 18 h at RT, the mixture was diluted with AcOEt, washed twice with water and brine. The organic layers were dried over $MgSO_4$, filtered, evaporated and chromatographied (silica gel, AcOEt/heptane, 1/1) to give the title compound (450 mg, 70%).

Step C]: rac-4-tert-Butoxycarbonylamino-1-(3,4-dimethoxy-phenyl)-piperidine-3-carboxylic acid ethyl ester A solution of rac-4-amino-1-(3,4-dimethoxy-phenyl)-piperidine-3-carboxylic acid ethyl ester (6.47 g) and $Boc_2O$ (5.02 g) in 50 ml $CH_2Cl_2$ was stirred 24 h at RT, then diluted with AcOEt, washed with water and brine. The organic layers were dried over $MgSO_4$, filtered, evaporated and chromatographied (silica gel, AcOEt/heptane, 1/1) to leave the title compound as a mixture of cis- and trans-diastereomers (4.50 g, 53%). MS: 409.4 $(M+H)^+$ Step D]: rac-4-tert-Butoxycarbonylamino-1-(3,4-dimethoxy-phenyl)-piperidine-3-carboxylic acid To a solution of rac-4-tert-butoxycarbonylamino-1-(3,4-dimethoxy-phenyl)-piperidine-3-carboxylic acid ethyl ester (170 mg) in 2 ml THF, were added 1 ml NaOH 1M and lithium hydroxide (100 mg). The suspension was stirred 22 h at RT., diluted with water and extracted twice with tert-butylmethylether. The aqueous layer was acidified to pH 4, saturated with NaCl and then the product was extracted with 3 portions of AcOEt. The organic layers were dried over $MgSO_4$, filtered, evaporated and chromatographed (silica gel, AcOEt) to provide the title compound (38 mg, 55%). MS: 381.3 $(M+H)^+$ Step E]: [(3S,4R) and (3R,4S)-1-(3,4-Dimethoxy-phenyl)-3-(thiazolidine-3-carbonyl)-piperidine-4-yl]-carbamic acid tert-butyl ester and [(3S,4S) and (3R,4R)-1-(3,4-Dimethoxy-phenyl)-3-(thiazolidine-3-carbonyl)-piperidine-4-yl]-carbamic acid tert-butyl ester To a solution of rac-4-tert-butoxycarbonylamino-1-(3,4-dimethoxy-phenyl)-piperidine-3-carboxylic acid (200 mg) in acetonitrile (5 ml) under ice cooling was added Hunig's base (0.5 ml), EDCI (191 mg), HOBT (135 mg) and thiazolidine (0.3 ml). The reaction mixture was stirred 3 h at 0° C. and kept at RT for 24 h, diluted with AcOEt, washed with 5% $NaHCO_3$ and brine, dried over magnesium sulfate and concentrated. The crude product was purified by chromatography on silica gel using AcOEt to give [(3S,4R) and (3R,4S)-1-(3,4-dimethoxy-phenyl)-3-(thiazolidine-3-carbonyl)-piperidine-4-yl]-carbamic acid tert-butyl ester (73 mg) and [(3S,4S) and (3R,4R)-1-(3,4-dimethoxy-phenyl)-3-(thiazolidine-3-carbonyl)-piperidine-4-yl]-carbamic acid tert-butyl ester (81 mg). MS: $(M+H)^+$ 452.4.

Step F]: [(3S,4R) and (3R,4S)-4-Amino-1-(3,4-dimethoxy-phenyl)-piperidine-3-yl]-thiazolidin-3-yl-methanone

[(3S,4R) and (3R,4S)-1-(3,4-Dimethoxy-phenyl)-3-(thiazolidine-3-carbonyl)-piperidine-4-yl]-carbamic acid tert-butyl ester (50 mg) was treated with 2 ml TFA for one hour at 0° C. The reaction mixture was diluted with AcOEt, washed with NaOH 1M and brine, the organic layers were dried over $MgSO_4$, filtered, evaporated and chromatographed (Isolute Flash SPE NH2, AcOEt) to give [(3S,4R) and (3R,4S)-4-Amino-1-(3,4-dimethoxy-phenyl)-piperidine-3-yl]-thiazolidin-3-yl-methanone (23 mg). MS: 352.1 $(M+H)^+$ NMR: (DMSO, 1H, 400 MHz, δ, TMS, 110° C.) 1.70-1.78 (m, 1H), 1.80-1.90 (m, 1H), 2.98-3.04 (m, 3H), 3.12-3.20 (m, 3H), 3.27-3.36 (m, 2H), 3.68 (s, 3H), 3.76 (s, 3H), 3.74-3.80 (m, 2H), 4.55 (d, 2H), 6.42 (dd, 1H), 6.55 (d, 1H), 6.79 (d, 1H).

Example 41

3 [(3S,4S) and (3R,4R)-4-Amino-1-(3,4-dimethoxy-phenyl)-piperidine-3-yl]-thiazolidin-3-yl-methanone This material was obtained from the racemic trans-isomer, isolated in example 40, step E, using the same procedure as in example 40, step F, to give 28 mg of the title compound. MS: 352.1 $(M+H)^+$ NMR: (DMSO, 1H, 400 MHz, 6, TMS, 110° C.) 1.40-1.55 (m, 1H), 1.78-1.86 (m, 1H), 2.55-2.90 (m, 4H), 2.90-3.01 (m, 1H), 3.03 (t, 2H), 3.50-3.60 (m, 2H), 3.68 (s, 3H), 3.76 (s, 3H), 3.74-3.90 (2m, 2H), 4.59-4.65 (m, 2H), 6.42 (dd, 1H), 6.56 (d, 1H), 6.79 (d, 1H).

Example 42

3 [(3S,4S) and (3R,4R)-4-Amino-1-(3,4-dimethoxy-phenyl)-piperidine-3-yl]-(2,5-dihydropyrrol-1-yl)-3-yl-methanone This material was prepared in analogy to example 40, steps E and F, using 2,5-dihydro-pyrrole. MS: 332.2 $(M+H)^+$ Example 43

3[(3S,4R) and (3R,4S)-4-Amino-1-(3,4-dimethoxy-phenyl)-piperidine-3-yl]-(2,5-dihydropyrrol-1-yl)-3-yl-methanone This material was prepared in analogy to example 40, steps E and F, using 2,5-dihydro-pyrrole. MS: 332.2 $(M+H)^+$ Example 44

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example 45

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 46

Injection solutions can have the following composition:

| Ingredients | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example 47

Soft gelatin capsules containing the following ingredients can be manufactured in a conventional manner:

| Ingredients | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85 % | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 48

Sachets containing the following ingredients can be manufactured in a conventional manner:

| Ingredients | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:
1. A compound of the formula I:

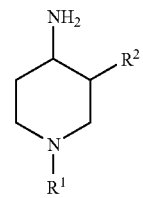

wherein:
R$^1$ is selected from the group consisting of phenyl, unsubstituted or mono-, di-, or trisubstituted, independently, by lower alkyl, lower alkoxy, phenyl, phenoxy, halogen, or lower halogenalkyl; and —(CHR$^3$)$_m$-phenyl, wherein m is 1, 2, or 3 and phenyl being unsubstituted or mono-, di, or trisubstituted, independently, by lower alkyl, halogen, lower halogenalkyl, lower alkoxy, phenyl or phenoxy and wherein R$^3$ is hydrogen, lower alkyl or phenyl;
R$_2$ is selected from the group consisting of phenyl, unsubstituted or mono-, di-, or trisubstituted, independently, by lower alkyl, halogen, lower halogenalkyl, or lower alkoxy; naphthyl, unsubstituted or mono-, di-, or trisubstituted, independently, by lower alkyl, halogen, lower halogenalkyl, or lower alkoxy; and pharmaceutically acceptable salts thereof, provided that 1-benzyl-3-(3,4-dimethoxyphenyl)-4-piperidylamine and 1-benzyl-3-phenyl-4-piperidylamine are excluded.

2. The compound according to claim 1, wherein R$^1$ is selected from the group consisting of phenyl, unsubstituted or mono-, di-, or trisubstituted, independently, by lower alkyl, halogen, lower halogenalkyl, lower alkoxy, phenyl or phenoxy; and —(CHR$^3$)$_m$-phenyl, wherein m is 1 or 2 and with phenyl being unsubstituted or mono-, di-, or trisubstituted, independently, by lower alkyl, halogen, lower halogenalkyl, lower alkoxy, phenyl or phenoxy and wherein R$^3$ is hydrogen.

3. The compound according to claim 1, wherein R$^1$ is selected from the group consisting of phenyl, unsubstituted or mono-, di-, or trisubstituted, independently, by lower alkyl, halogen, lower halogenalkyl, lower alkoxy, phenyl or phenoxy; and —(CHR³)ₘ-phenyl, wherein m is 1 or 2 and with phenyl being unsubstituted or mono-, di-, or trisubstituted by lower alkoxy and wherein R³ hydrogen.

4. The compound according to claim 1, wherein R¹ is phenyl mono-, di-, or trisubstituted, independently, by lower alkyl, halogen, lower halogenalkyl, lower alkoxy, phenyl or phenoxy.

5. The compound according to claim 1, wherein R² is selected from the group consisting of phenyl, unsubstituted or mono-, di-, or trisubstituted, independently, by lower alkyl, halogen, lower halogenalkyl, or lower alkoxy.

6. The compound according to claim 1, wherein R² is phenyl, unsubstituted or mono-, di-, or trisubstituted, independently, by lower alkyl, halogen, halogenalkyl, or lower alkoxy.

7. The compound according to claim 1, selected from (cis)-3-phenyl-1-phenethyl-piperidine-4-yl-amine, (trans)-3-phenyl-1-phenethyl-piperidine-4-yl-amine, (cis)-3-(3-chloro-phenyl)-1-phenethyl-piperidine-4-yl-amine, (cis/trans)-3-(3-chloro-phenyl)-1-benzyl-piperidine-4-yl-amine, (cis/trans)-3-(3-methyl-phenyl)-1-benzyl-piperidine-4-yl-amine, (cis)-3-(3-chloro-phenyl)-1-[2-(3,4-dimethoxy-phenyl)-ethyl]-piperidine-4-yl-amine, (cis)-3-o-tolyl-1-(3,4,5-trimethoxy-phenyl)-piperidine-4-yl-amine hydrochloride, (trans)-3-o-tolyl-1-(3,4,5-trimethoxy-phenyl)-piperidine-4-yl-amine hydrochloride, (cis/trans)-3-o-tolyl-1-(3,4,5-trimethoxy-phenyl)-piperidine-4-yl-amine hydrochloride, (cis/trans)-1-(3,4-dimethoxy-phenyl)-3-m-tolyl-piperidine-4-yl-amine hydrochloride, (cis/trans)-1-(3,4-dimethoxy-phenyl)-3-p-tolyl-piperidine-4-yl-amine hydrochloride, (cis/trans)-1-(3,4-dimethoxy-phenyl)-3-(3,4-dimethyl-phenyl)-piperidine-4-yl-amine hydrochloride, (cis/trans)-1-(3,4-dimethoxy-phenyl)-3-(3-methoxy-phenyl)-piperidine-4-yl-amine hydrochloride, and pharmaceutically acceptable salts thereof 8. The compound according to claim 1, selected from (cis)-3-phenyl-1-phenethyl-piperidine-4-yl-amine, (cis)-3-(3-chloro-phenyl)-1-phenethyl-piperidine-4-yl-amine, (cis/trans)-3-(3-chloro-phenyl)-1-benzyl-piperidine-4-yl-amine, (cis/trans)-3-(3-methyl-phenyl)-1-benzyl-piperidine-4-yl-amine, (cis)-3-(3-chloro-phenyl)-1-[2-(3,4-dimethoxy-phenyl)-ethyl]-piperidine-4-yl-amine, (trans)-3-o-tolyl-1-(3,4,5-trimethoxy-phenyl)-piperidine-4-yl-amine hydrochloride, (cis/trans)-3-o-tolyl-1-(3,4,5-trimethoxy-phenyl)-piperidine-4-yl-amine hydrochloride, (cis/trans)-1-(3,4-dimethoxy-phenyl)-3-m-tolyl-piperidine-4-yl-amine hydrochloride, and pharmaceutically acceptable salts thereof.

9. The compound according to claim 1, selected from (cis)-3-(3-chloro-phenyl)-1-phenethyl-piperidine-4-yl-amine, (cis/trans)-3-(3-chloro-phenyl)-1-benzyl-piperidine-4-yl-amine, (cis/trans)-3-(3-chloro-phenyl)-1-[2-(3,4-dimethoxy-phenyl)-ethyl]-piperidine-4-yl-amine, (cis)-1-(3,4-dimethoxy-phenyl)-3-m-tolyl-piperidine-4-yl-amine hydrochloride, and pharmaceutically acceptable salts thereof.

10. A process for the manufacture of compounds of formula I according to claim 1, comprising the steps of:
a) converting a compound of the formula

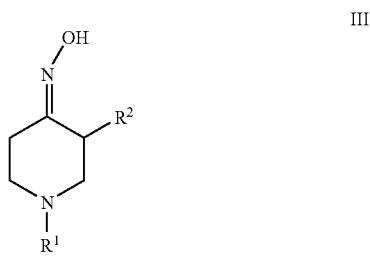

II wherein R¹ and R² are as defined in claim 1, with hydroxylamine or a salt thereof into an oxime of the formula

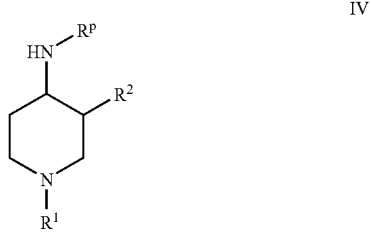

III wherein R¹ and R² are as defined in claim 1, and further reducing the oxime of formula III by catalytic hydrogenation or alternatively by a reduction with a metal hydride into the compound of formula I; or b) deprotecting an 4-aminopiperidine derivative of the formula

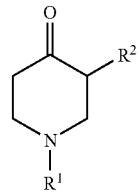

IV wherein R¹ and R² are as defined before and Rᵖ is an amino protecting group.

11. A pharmaceutical composition, comprising a therapeutically effective amount of a compound according to claim 1 and a pharmaceutically acceptable carrier and/or adjuvant.

* * * * *